United States Patent [19]
Heymes et al.

[11] Patent Number: 5,336,776
[45] Date of Patent: Aug. 9, 1994

[54] NOVEL 3-ACETOXYMETHYL-7-(IMINOACETAMIDO)-CEPHALOSPORANIC ACID

[75] Inventors: René Heymes, Romainville; Andr Lutz, Strasbourg, both of France

[73] Assignee: Roussel UCLAF, France

[21] Appl. No.: 777,614

[22] Filed: Oct. 16, 1991

Related U.S. Application Data

[60] Division of Ser. No. 582,386, Sep. 13, 1990, Pat. No. 5,103,012, which is a division of Ser. No. 359,870, May 31, 1989, Pat. No. 4,988,811, which is a division of Ser. No. 181,658, Apr. 14, 1988, abandoned, which is a division of Ser. No. 449,680, Dec. 14, 1982, Pat. No. 4,843,164, which is a division of Ser. No. 257,984, Apr. 23, 1981, Pat. No. 4,376,203, which is a division of Ser. No. 71,295, Aug. 30, 1979, abandoned, which is a division of Ser. No. 917,985, Jun. 22, 1978, Pat. No. 4,283,396, which is a division of Ser. No. 817,114, Jul. 13, 1977, Pat. No. 4,152,432, which is a continuation-in-part of Ser. No. 761,270, Jan. 21, 1977, abandoned.

[30] Foreign Application Priority Data

Jun. 11, 1976 [FR] France .................. 76 07307
Jun. 23, 1976 [FR] France .................. 76 25651
Jul. 11, 1976 [FR] France .................. 76 01834
Aug. 18, 1979 [FR] France .................. 76 17743

[51] Int. Cl.$^5$ .......................... C07D 277/593
[52] U.S. Cl. ..................... 548/194; 548/195
[58] Field of Search ................... 548/194, 195

[56] References Cited

U.S. PATENT DOCUMENTS

| | | | |
|---|---|---|---|
| 4,166,115 | 8/1979 | Takaya | 548/194 |
| 4,203,899 | 5/1980 | Ochiai | 548/194 |
| 4,376,203 | 3/1983 | Heymes | 548/194 |
| 5,103,012 | 4/1992 | Heymes | 548/194 |

Primary Examiner—Robert Gerstl
Attorney, Agent, or Firm—Bierman and Muserlian

[57] ABSTRACT

Thiazole intermediates for Cephalosporing are prepared.

1 Claim, No Drawings

NOVEL 3-ACETOXYMETHYL-7-(IMINOACETAMIDO)-CEPHALOSPORANIC ACID

PRIOR APPLICATION

This application is a division of U.S. patent application Ser. No. 582,386 filed Sep. 13, 1990, now U.S. Pat. No. 5,103,012 which is a division of patent application Ser. No. 359,870 filed May 31, 1989, now U.S. Pat. No. 4,988,811 which is a division of U.S. patent application Ser. No. 181,658 filed Apr. 14, 1988, now abandoned, which is a division of U.S. patent application Ser. No. 449,680 filed Dec. 14, 1982, now U.S. Pat. No. 4,843,164 which is a division of U.S. patent application Ser. No. 257,984 filed Apr. 23, 1981, now U.S. Pat. 4,376,203 which is a division of U.S. patent application Ser. No. 071,295 filed Aug. 30, 1979, now abandoned, which is a division of U.S. patent application Ser. No. 917,985 filed Jun. 22, 1978, now U.S. Pat. No. 4,283,396 which is a division of U.S. patent application Ser. No. 817,114 filed Jul. 13, 1977, now U.S. Pat. No. 4,152,432, which is a continuation-in-part of copending commonly assigned U.S. patent application Ser. No. 761,270 filed Jan. 21, 1977, now abandoned.

STATE OF THE ART

French patents No. 2,137,899, No. 2,137,900, No. 2,123,545 and No. 2,294,690 relate to 3-acetoxymethyl-7-amino-cephalosporanic acid compounds.

OBJECTS OF THE INVENTION

It is an object of the invention to provide the novel cephalosporanic acid derivatives of formula I and novel processes and intermediates for their preparation.

It is another object of the invention to provide novel antibiotic compositions and a novel method of combatting bacterial infections in warm-blooded animals.

These and other objects and advantages of the invention will become obvious from the following detailed description.

THE INVENTION

The novel 3-acetoxymethyl-7-(iminoacetamido)-cephalosporanic acid derivatives of the invention have the formula

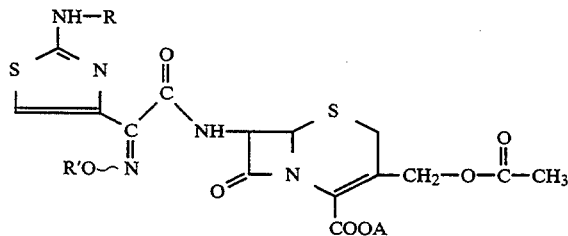

I wherein R is selected from the group consisting of hydrogen and groups easily removable by acid hydrolysis or hydrogenolysis, R' is selected from the group consisting of hydrogen, alkyl of 1 to 4 carbon atoms, alkenyl and alkynyl of 2 to 4 carbon atoms and groups easily removable by acid hydrolysis or hydrogenolysis, A is selected from the group consisting of hydrogen, alkali metal and equivalents of an alkaline earth metal or magnesium and an organic amine base with the provision that when R' is a group easily removable by acid hydrolysis or hydrogenolysis, R is also and when R' is hydrogen, R also is hydrogen and the wavy line means the OR' group may be in either one of the two possible syn or anti positions.

The groups easily removable by acid hydrolysis or by hydrogenolysis are well known in cephalosporin chemistry and examples thereof are tert.-butoxycarbonyl, trityl, benzyl, dibenzyl, trichloroethyl, carbobenzyloxy, formyl, trichloroethoxycarbonyl or 2-tetrahydropyranyl. R' may also be alkyl, alkenyl or alkynyl such as methyl, ethyl, propyl, isopropyl, butyl, sec.-butyl, tert.-butyl, vinyl, propenyl, butenyl, ethynyl or propargyl.

Examples of A are hydrogen, potassium, sodium, lithium, calcium, magnesium, trimethylamine, triethylamine, methylamine, propylamine, N,N-dimethylethanolamine, tris-(hydroxymethyl)-aminomethane, arginine or lysine.

The groups easily removable by acid hydrolysis or hydrogenolysis that are preferred are tert.-butoxycarbonyl, trityl, dibenzyl, trichloroethyl and carbobenzyloxy.

The compounds of formula I may exist in the form of the syn isomer of the formula

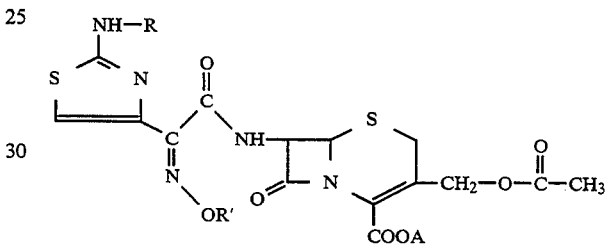

or in the form of the anti isomer of the formula

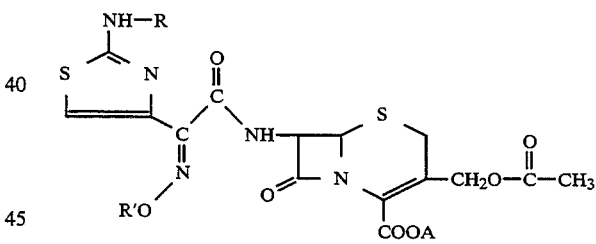

but the OR' group is preferably in the syn position.

Preferably, in the compounds of formula I, R is hydrogen or trityl, R' is hydrogen, trityl, alkyl of 1 to 4 carbon atoms or alkenyl or alkynyl of 2 to 4 carbon atoms and A is hydrogen, sodium or diethylamine.

Preferred compounds of formula I are 3-acetoxymethyl -7-[2-(2-amino-4-thiazolyl)-2-methoxyiminoacetamido]-ceph-3-eme-4-carboxylic acid, sodium 3-acetoxymethyl-7-[2-(2-amino-4-thiazolyl)-2-methoxyiminoacetamido]-ceph-3-eme-4-carboxylate, syn isomer of 3-acetoxymethyl-7-[2-(2-amino-4-thiazolyl)-2-methoxyiminoacetamido]-ceph-3-eme-4-carboxylic acid, syn isomer of sodium 3-acetoxymethyl-7-[2-(2-amino-4-thiazolyl)-2-methoxyiminoacetamido]-ceph-3-eme-4-carboxylate, 3-acetoxymethyl-7-[2-(2-amino-4-thiazolyl)-2-methoxyiminoacetamido]-ceph-3-eme-4-carboxylic acid as obtained by the process described in Example 4, sodium 3-acetoxymethyl-7-[2-(2-amino-4-thiazolyl)-2-methoxyiminoacetamido]-ceph-3-eme-4-carboxylate as obtained by the process described in Example 7, syn isomer of cristalline sodium 3-acetoxymethyl-7-[2-(2-amino-4-thiazolyl)-2-methox-yiminoacetamido]-ceph-3-eme-4-carboxylate, syn isomer of 3-acetoxymethyl-7-[2-(2-amino-4-thiazolyl)-2-ethoxyiminoacetamido]-ceph-3-eme-4-carboxylic acid and its alkali metal, alkaline earth metal, magnesium and organic amine salts syn isomer of 3-acetoxymethyl-7-[2-(2-amino-4-thiazolyl)-2-(2-propenyloxyimino)-acetamido]-ceph-3-eme-4-carboxylic acid and its alkali metal, alkaline earth metal, magnesium and organic amine salts, syn isomer of 3-acetoxymethyl-7-(2-(2-amino-4-thiazolyl)-2-(1-methylethoxyimino)-acetamido)-ceph-3-eme-4-carboxylic acid and its alkali metal, alkaline earth metal, magnesium and organic amine salts and syn isomer of 7-(2-(2-amino-4-thiazolyl)-2-hydroxyiminoacetamido)-3-acetoxymethyl-ceph-3-eme-4-carboxylic acid and their alkali metal, alkaline earth metal, magnesium and organic amine salt especially the sodium salt and syn isomer of 7-(2-(2-trityl amino-4-thiazolyl)-2-tritylhydroxyimino acetamido)-3-acetoxymethyl-ceph-3-eme-4-carboxylic acid.

The products of the invention may exist in the form indicated in formula I or in the form of products of the formula

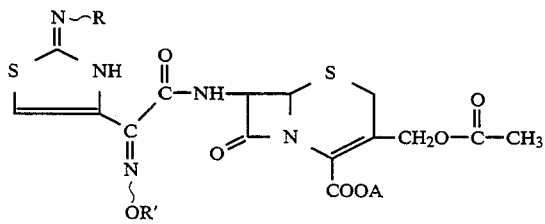

The process of the invention for the preparation of the compounds of formula I comprises reacting 7-amino-cephalosporanic acid with an acid of the formula

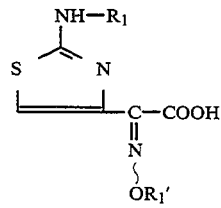

or a derivative thereof wherein $R_1$ is a group easily removable by acid hydrolysis or hydrogenolysis and $R_1'$ is selected from the group consisting of alkyl of 1 to 4 carbon atoms, alkenyl and alkynyl of 2 to 4 carbon atoms and a group easily removable by acid hydrolysis or hydrogenolysis to form a compound of the formula

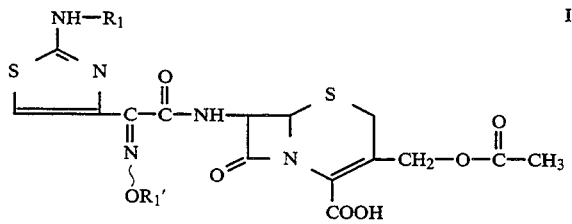

and the latter may be subjected to acid hydrolysis or hydrogenolysis to obtain a compound of formula I wherein R and A are hydrogen and R' is hydrogen, alkyl of 1 to 4 carbon atoms or alkenyl or alkynyl of 2 to 4 carbon atoms and the said product Ia or I may be satified by known methods.

In a preferred mode of the said process, 7-amino-cephalosporanic acid is reacted with a functional derivative of the acid of formula II such as the acid chloride or anhydride such as that formed in situ with isobutyl chloroformate or dicyclohexylcarbodiimide with the acid. Other acid halides other acid anhydrides formed in situ with other alkyl chloroformates, a dialkylcarbodiimide or other dicycloalkylcarbodiimide may be used. Equally useful are other acid derivatives such as the acid azide, active amide or ester of the acid such as formed by hydroxysuccimide, p-nitrophenol or 2,4-dinitrophenol.

The reaction of 7-amino-cephalosporanic acid with isobutyl chloroformate anhydride or acid chloride of the acid of formula II is preferably effected in the presence of a basic agent such as an alkali metal carbonate or an organic tertiary amine such as N-methyl-morpholine or pyridine or a trialkylamine such as triethylamine.

The acid hydrolysis may be effected with formic acid, trifluoroacetic acid or acetic acid and may be anhydrous or in aqueous solution. Also useful is zinc-acetic acid system. To eliminate tert.-butoxycarbonyl or trityl groups, the acid agent is preferably anhydrous trifluoroacetic acid or aqueous acetic acid or formic acid. The zinc-acetic acid system is preferably used to remove a trichloroethyl group. The benzyl, dibenzyl and carbobenzyloxy groups are preferably removed by hydrogenolysis in the presence of a hydrogenation catalyst.

The salification may be effected by known methods such as by reacting the free acid with a mineral base such as sodium hydroxide, potassium hydroxide or sodium bicarbonate or a salt of a substituted or non-substituted aliphatic carboxylic acid such as diethylacetic acid, ethylhexanoic acid or especially acetic acid with the preferred salts being the sodium salts. The salification may be effected with an organic base such as triethylamine.

For the preparation of the salts, the solvates of the free acids may also be used in place of the free acids. The solvates may be obtained with water, formic acid or an alcohol, for example. The solvates with an alcohol, preferably ethanol, may be obtained by treatment with an alcohol-water mixture of the solvate with formic acid which is then followed by concentration of the solution.

The salification is preferably effected in at least one solvent such as water, ether, methanol, ethanol or acetone and the salts may be either crystalline or amorphous depending on the reaction conditions used. The crystalline salts are preferably prepared by reacting the free acid or a solvate thereof, formed for example with formic acid or ethanol, with a salt of the above mentioned aliphatic carboxylic acid, preferably sodium acetate. In the preparation of a sodium salt, the reaction is effected in the appropriate organic solvent such as methanol which can contain small amounts of water. It is also possible to change the amorphous salts into crystalline salts. To this effect, an amorphous sodium salt which can be in the form of a solvate with, for example, 0.5, 1 or 1.5 moles of water is dissolved in an appropriate organic solvent, preferably a low molecular weight alcohol such as methanol. Crystallization may then be directly effected or by addition of other solvents such as ethanol, isopropanol, n-butanol, acetone, ethers and generally organic solvents miscible with methanol. If the starting material or the solvent or the two constituents contain water, the salt may crystallize in the form of a hydrate. For example, the syn isomer of sodium 3-acetoxymethyl-7-[2-(2-amino-4-thiazolyl)-2-methoxyiminoacetamido]-ceph-3-eme-4-carboxylate has been isolated with 0.5, 1 or 1.5 moles of water.

In a modification of the process of the invention to prepare a compound of the formula

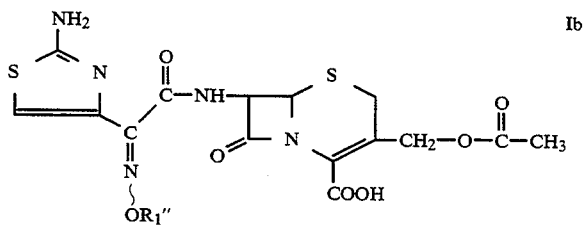

wherein $R_1''$ is selected from the group consisting of hydrogen alkyl of 1 to 4 carbon atoms and alkenyl and alkynyl of 2 to carbon atoms, a compound of the formula

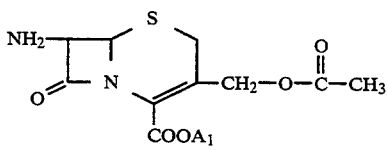

wherein $A_1$ is a group easily removable by acid hydrolysis or hydrogenolysis is reacted with an acid of formula II or a function derivative thereof wherein $R_1'$ is chloroacetyl or a group easily removable by acid hydrolysis or hydrogenolysis or alkyl of 1 to 4 carbon atoms or alkenyl or alkynyl of 2 to 4 carbon atoms and $R_1$ is chloroacetyl or a group easily removable by acid hydrolysis or hydrogenolysis to obtain a compound of the formula

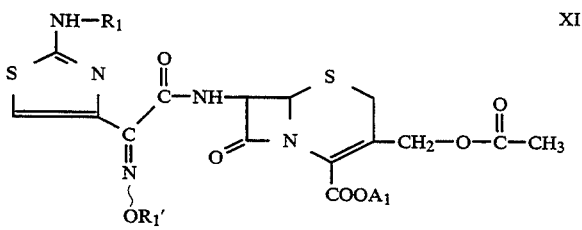

which is then treated with one or more acid hydrolysis agent or one or more hydrogenolysis agents or with thiourea or with one or more of these different agents to recover a compound of formule Ib.

Examples of groups easily removable by acid hydrolysis or hydrogenolysis for $R_1$ or $R_1'$ are tert.-butozycarbonyl, trityl, benzyl, dibenzyl, trichloroethyl, carbobenzyloxy, or formyl but also useful are 2-tetrahydropyranyl and trichloroethoxycarbonyl. For $A_1$, the groups are preferably benzhydryl, tert.-butyl, benzyl, p-methoxybenzyl or trichloroethyl.

In a preferred mode of this process, a compound of formula Ic is reacted with a functional derivative of the acid of formula II such as the acid chloride or acid anhydride such as that formed in situ with isobutyl chloroformate or dicyclohexylcarbodiimide. Equally useful are other acid halides or other mixed anhydrides formed in situ with other alkyl chloroformates or other dicycloalkylcarbodiimides or a dialkylcarbodiimide. Equally useful are other acid derivative such as acid azide, active amides of the acid or active ester of the acid such as that formed with hydroxy succinimide, p-nitrophenol or 2,4-dinitrophenol. When the acid halide or acid anhydride with isobutyl chloroformate are used, it is preferred to effect the reaction in the presence of a basic agent such as an alkali metal carbonate or a tertiary organic amine such as N-methyl morpholine, pyridine or a trialkylamine such as triethylamine.

The compounds of formula XI are changed into compounds of formula Ib wherein $R_1$ and $A_1$ are substituents replaced by hydrogen and when $R_1'$ is a group easily removed by acid hydrolysis or hydrogenolysis or is chloroacetyl, the compounds of formula XI are changed to compounds of formula Ib when $R_1'$ is replaced by hydrogen. To accomplish this, the compound of formula XI is treated with one or more acid hydrolysis agents when $R_1$ and $A_1$ are a group easily removed by acid hydrolysis and $R_1'$ is a group easily removed by acid hydrolysis or alkyl or with one or more hydrogenolysis agents when $R_1$ and $A_1$ are groups easily removed by hydrogenolysis and $R'_1$ is a group easily removed by hydrogenolysis or alkyl. The compounds of formula XI are treated with one or more acid hydrolysis agents and one or more hydrogenolysis agents when at least one of $R_1$, $A_1$ and $R'_1$ is a group easily removed by acid hydrolysis and at least one of these groups is a group easily removed by hydrogenolysis. Finally, the compound of formula XI is treated with thiourea and optional with one or more acid hydrolysis agents or hydrogenolysis agents, when at least one of $R_1$ and $R'_1$ is chloroacetyl.

The acid hydrolysis may be effected with formic acid, trifluoroacetic acid or acetic acid and may be anhydrous or in aqueous solution. Also useful is zinc-acetic acid system. To eliminate tert-butoxycarbonyl or trityl groups for $R_1$ or $R'_1$ or benzyhydryl, tert.-butyl or paramethoxy benzyl for $A_1$, the acid agent is preferably anhydrous trifluoroacetic acid or aqueous acetic acid or formic acid. The zinc-acetic acid system is preferably used to remove a trichloroethyl group for $R_1$, $R'_1$ and $A_1$. The benzyl, dibenz and carbobenzyloxy groups for $R_1$ and $R'_1$ and benzyl for $R_1$, $R'_1$ and $A_1$ are preferably removed by hydrogenolysis such as with hydrogen in the presence of a hydrogenation catalyst. The reaction of thiourea with a compound of formula XI containing at least one chloroacetyl is preferably effected in a neutral or acid media as described by Nasaki (J.A.C.S., Vol. 90 (1968), p. 4508).

Another aspect of the invention includes the process for the preparation of compounds of formula II by reacting thiourea with a compound of the formula

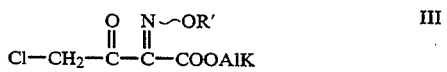

wherein $R'$ has the above definition and AlK is alkyl of 1 to 4 carbon atoms and treating the resulting product with a base to form a compound of the formula

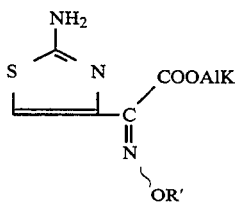

reacting the latter with a functional derivative of a group easily removable by acid hydrolysis or hydrogenolysis to obtain a compound of the formula

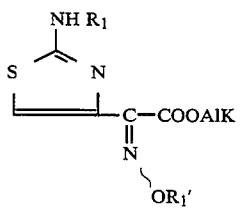

wherein $R_1$ and $R_1'$ have the above definitions and treating the latter with a base and then an acid to obtain the corresponding compound of formula II.

Preferably, the base used to treat the compound of formula IV is potassium acetate but other bases such as alkali metal carbonates or bicarbonates or dilute sodium hydroxide or potassium hydroxide are also useful. The functional derivative of a group which is easily removable by acid hydrolysis or hydrogenolysis is preferably trityl chloride in the presence of triethylamine or other tertiary amine bases such as pyridine, N-methyl-morpholine or other trialkylamines. Equally useful are tert.-butyl chloroformate formed in situ, tert.-butyl azido formate, trichloroethyl chloroformate, benzyl chloroformate, mixed formyl-acetic acid anhydride prepared in situ, benzyl and dibenzyl halides such as the chloride, phthalic anhydride or N-carbethoxyphthalimide.

The base used to treat the compound of formula V is preferably sodium hydroxide but other bases such as potassium hydroxide or barium hydroxide are also useful. The acid used to obtain the compound of formula II is preferably dilute hydrochloric acid but other acids such as acetic acid or formic acid may also be used.

In a variation of the process to produce compounds of formula II, a compound of formula IV is treated first with a base and then with an acid to obtain a compound of the formula

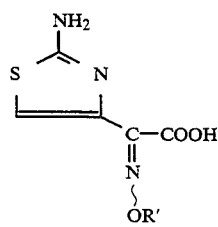

and reacting the latter with a functional derivative of $R_1$ wherein $R_1$ is chloroacetyl or a group easily removably by acid hydrolysis or hydrogenolysis to obtain the corresponding compound of formula II.

The base used for the saponification is preferably sodium hydroxide but equally useful are potassium hydroxide and barium hydroxide. The preferred acid is dilute hydrochloric acid but also useful are acetic acid or formic acid. The functional derivative of $R_1$ is preferably trityl chloride used in the presence of triethylamine or other tertiary amine bases such as other trialkylamines, pyridine or N-methyl-morpholine. Equally useful are other easily removable groups functional derivatives such as tert.-butyl chloroformate formed in situ or tert.-butyl azidoformate, trichloroethyl chloroformate or benzyl chloroformate, or a mixed formylacetic acid anhydride prepared in situ, benzyl or dibenzyl chloride or other halide, phthalic anhydride or N-carbethoxyphthalimide. The functional derivative of chloroacetyl is preferably chloroacetic acid anhydride or a halide such as monochloroacetyl chloride and in the latter case, a base as defined above is preferably present.

Another feature of the invention is a process for the preparation of a compound of the formula

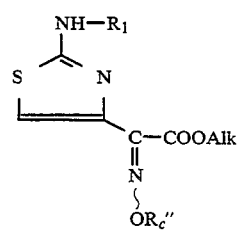

wherein $R_1$ and $R_c''$ are chloroacetyl or a group easily removed by acid hydrolysis or hydrogenolysis without being the same and Alk is alkyl of 1 to 4 carbon atoms comprising reacting a compound of the formula

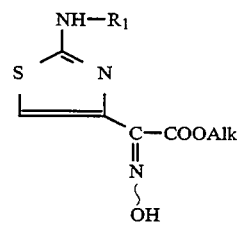

with a functional derivative of $R_c''$. $R_1$ is preferably trityl and the functional derivative of $R_c''$ is preferably dihydropyranyl to form the tetrahydropyranyl compound.

In a variation of the process of the invention to prepare compounds of formula I wherein A and R are hydrogen and R' is hydrogen, alkyl of 1 to 4 carbon atoms or alkenyl or alkynyl of 2 to 4 carbon atoms, a salt of a compound of formula Ia wherein-$R_1$ is a group easily removable by acid hydrolysis and $R_1'$ is selected from the group consisting of alkyl of 1 to 4 carbon atoms, alkenyl or alkynyl of 2 to 4 carbon atoms and a group easily removable by acid hydrolysis is treated with an acid to obtain the desired compound or a salt of a compound of formula Ia wherein $R_1$ is a group easily removable by hydrogenolysis and $R_1'$ is selected from the group consisting of alkyl of 1 to 4 carbon atoms, alkenyl or alkynyl of 2 to 4 carbon atoms and a group easily removable by hydrogenolysis is subjected to hydrogenolysis to obtain the desired compound in the form of a salt. The preferred acid is formic acid but also useful are trifluoroacetic acid or acetic acid in anhydrous or aqueous solution form. The hydrogenolysis is preferably effected with a hydrogenation catalyst.

A variation of the process to prepare a compound of the formula

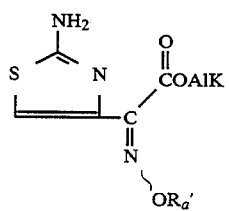 IVa wherein Alk is alkyl of 1 to 4 carbon atoms and $R_a'$ is alkyl of 1 to 4 carbon atoms comprises reacting a compound of the formula

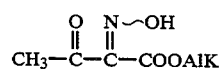 VI with an alkylation agent to obtain a compound of the formula

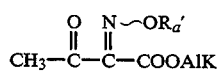 VII reacting the latter with a bromination agent to form a compound of the formula

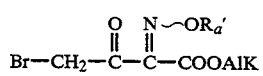 VIII and reacting the latter with thiourea and then a base to obtain the compound of formula IVa.

The alkylation agent used to treat the compound of formula VI is preferably an alkyl halide such as an alkyl chloride, bromide or iodide or an alkyl sulfate of 1 to 4 alkyl carbon atoms. The bromination agent reacted with the compound of formula VII is preferably bromine and the base used to obtain the product of formula IVa is preferably an alkali metal carbonate or bicarbonate but equally useful are dilute sodium or potassium hydroxide or potassium acetate.

A variation of the process to produce the compounds of formula I wherein A and R are hydrogen and R' is hydrogen, alkyl of 1 to 4 carbon atoms or alkenyl or alkynyl of 2 to 4 carbon atoms comprises reacting 7-amino-cephalosporanic acid with a compound of the formula

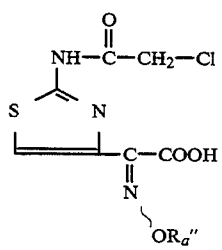 IIa wherein $R_a''$ is selected from the group consisting of chloroacetyl, alkyl of 1 to 4 carbon atoms and alkenyl and alkynyl of 2 to 4 carbon atoms or a functional derivative thereof to obtain a compound of the formula

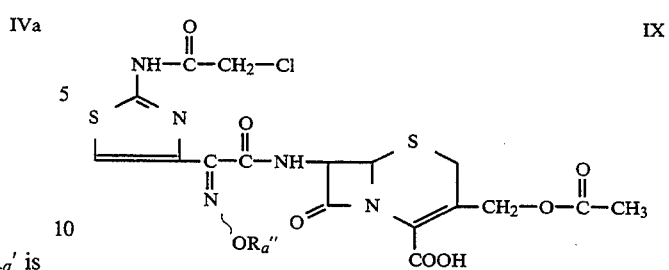 IX and reacting the latter with thiourea to obtain the corresponding compound of formula I.

The reaction with 7-amino-cephalosporanic acid is effected under the same conditions as the reaction with a compound of formula II. The reaction with thiourea is preferably effected in a neutral or acid media with the type of reaction described by Masaki [J.A.C.S., Vol. 90 (1968), p. 4508].

A process for the preparation of a compound of formula IIa comprises reacting a functional derivative of chloroacetic acid with a compound of the formula

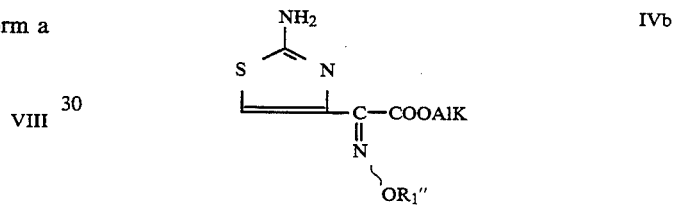 IVb wherein $R_1''$ is hydrogen, alkyl of 1 to 4 carbon atoms or alkenyl or alkynyl of 2 to 4 carbon atoms and alk is alkyl of 1 to 4 carbon atoms to obtain a compound of the formula

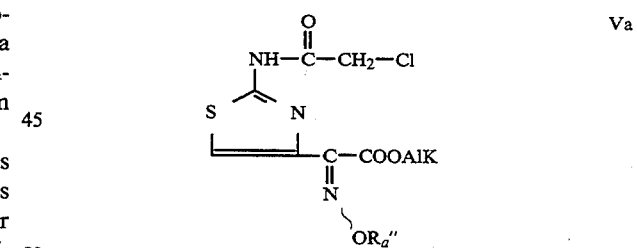 Va wherein $R_a''$ has the above definition and treating the latter with first a base and then an acid to obtain a compound of formula IIa.

The functional derivative of chloroacetic acid is preferably chloroacetic acid anhydride or chloroacetyl halide such as the chloride. If the acid halide is used, the reaction is preferably effected in the presence of a basic agent as discussed previously. The base used to treat the compound of formula Va is preferably sodium hydroxide but other bases such as potassium hydroxide or barium hydroxide may be used. The acid used to obtain a compound of formula IIa is preferably dilute hydrochloric acid but equally useful are acetic acid or formic acid.

A variant of the process to obtain a compound of the formula

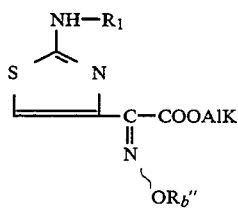

Vb wherein $R_1$ and AIK have the above definition and $R_b''$ is alkyl of 1 to 4 carbon atoms or alkenyl or alkynyl of 2 to 4 carbon atoms comprises treating a compound of the formula

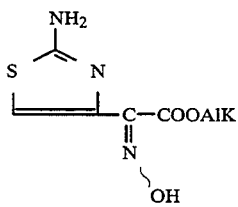

IV"

with a functional derivative of a group easily removable by acid hydrolysis or hydrogenolysis to obtain a compound of the formula

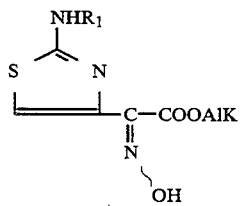

X and reacting the latter with an alkylation agent to obtain the compound of formula Vb.

The said functional derivative is preferably trityl chloride used in the presence of a base preferably triethylamine although other bases such as N-methyl-morpholine, pyridine or other trialkylamine may be used. Other useful functional derivatives are tert.-butyl chloroformate, tert.-butyl azidoformate, trichloroethyl chloroformate, dibenzyl chloroformate, mixed formylacetic acid anhydride formed in situ, benzyl halides and dibenzyl halides such as the chloride, phthalic anhydride or N-carbethoxyphthalimide. The alkylation agent is preferably an alkyl sulfate or an alkyl halide such as the iodide.

The syn and anti configuration of the products of formula I is determined by the configuration of the products of formula IV since the latter configuration is maintained in the synthesis. The same is true for the products of formula IVa, IVb and IV" as they are within the scope of formula IV. The configuration of the products of formula IV depends upon a certain number of parameters of the process to prepare the products.

It can also be stated that the action of thiourea with the products of formula III is effected either in an aqueous solvent such as aqueous acetone or aqueous ethanol or at room temperature with a substantially stoichiometric amount of thiourea stirred therewith for a reaction time of 1 to 3 hours or the said conditions can be combined to obtain the syn isomer.

The process of the invention for the preparation of compounds of formula IV in the syn form comprises reacting thiourea with a compound of the formula

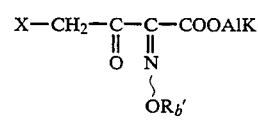

III' wherein X is chlorine or bromine, AIK is alkyl of 1 to 4 carbon atoms and $R_b'$ is selected from the group consisting of hydrogen, alkyl of 1 to 4 carbon atoms, alkenyl and alkynyl of 2 to 4 carbon atoms and a group easily removable by acid hydrolysis or hydrogenolysis when X is chlorine or hydrogen or alkyl of 1 to 4 carbon atoms when X is bromine either in an aqueous solvent, or at room temperature with a substantially stoichiometric amount of thiourea for a few hours, or by combination of the said conditions.

The antibiotic compositions of the invention are comprised of an antibiotically effective amount of at least one compound of formula I and an inert pharmaceutical carrier. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, latose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers. The compositions of the invention and particularly those containing the compounds of formula I in the syn form possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria Among the preferred compositions are those containing the compounds of formula I with the syn form. Preferably R is hydrogen R' is hydrogen, alkyl of 1 to 4 carbon atoms and alkenyl and alkynyl of 2 to 4 carbon atoms and A is hydrogen and sodium.

Among the preferred compositions are also those containing as active principle the following products:

3-acetoxymethyl 7-[2-(2-amino 4-thiazolyl) 2-methoxy imino acetamido] ceph-3-eme 4-carboxylic acid, syn isomer, this product is especially described in example 4, 6, 20 or 22, the sodium salt of 3-acetoxymethyl 7-[2-(2-amino-4-thiazolyl) 2-methoxy imino acetamido] ceph-3-eme 4-carboxylic acid, syn isomer, this product is especially described in example 7, the crystalline sodium salt of 3-acetoxymethyl 7-[2-(2-amino-4-thiazolyl)-2-methoxyiminoaetamido]- ceph-3-eme-4-carboxylic acid, syn isomer, or the following products:

3-acetoxymethyl-7-[2-(2-amino-4-thiazoyl)-2-ethoxyiminoacetamido]-ceph-3-eme-4-carboxylic acid, syn isomer and its pharmaceutically acceptable salts with an alkali metals, the alkaline-earth metals, magnesium or the organic amino base, 3-acetoxymethyl-7-[2-(2-amino-4-thiazolyl)-2-((2-propenyl)-oxyimino)-acetamido]-ceph-3-eme-4-carboxylic acid, syn isomer and its pharmaceutically acceptable salts with the alkali metals, the alkaline earth metals, magnesium or the organic amine bases, 3-acetoxymethyl-7-[2-(2-amino-4-thiazolyl)-2-((1-methylethoxy)-imino)-acetamido]-ceph-3-eme-4-carboxylic acid, syn isomer and its pharmaceutically acceptable salts with the alkali metals, the alkaline earth metals, magnesium or the organic amino bases, syn isomer of 7-[2-(2-amino-4-thiazolyl)-2-hydroxyimino-acetamido]-3-acetoxymethyl-ceph-3-eme-4-carboxylic acid and its non-toxic, pharmaceutically acceptable salts with alkali metals, alkaline earth metals, magnesium and organic amine bases and especially the free acid and its sodium salt.

The novel method of the invention for combatting bacterial infections in warm-blooded animals, including humans, comprises administering to warm-blooded animals an antibacterially effective amount of at least one compound of formula I. The compounds may be administered orally, rectally, parenterally or locally by topical application to the skin or mucous. The usual daily dose is 5 to 80 mg/kg depending on the compound and the method of administration.

Among the novel intermediate compounds of the invention are compounds of the formula

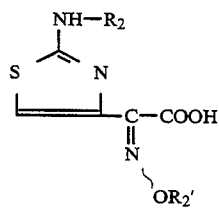

wherein $R_2$ is selected from the group consisting of hydrogen and a group easily removable by acid hydrolysis or hydrogenolysis and $R_2'$ is selected from the group consisting of hydrogen, alkyl of 1 to 4 carbon atoms, alkenyl and alkynyl of 2 to 4 carbon atoms and a group easily removable by acid hydrolysis or hydrogenolysis with the proviso that $R_2'$ is not hydrogen when $R_2$ is other than hydrogen and the novel compounds of the formula

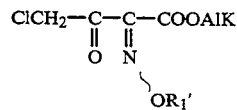

wherein AlK is alkyl of 1 to 4 carbon atoms and $R_1'$ is selected from the group consisting of alkyl of 1 to 4 carbon atoms, alkenyl and alkynyl of 2 to 4 carbon atoms and a group easily removable by acid hydrolysis or hydrogenolysis and the novel compounds of the formula

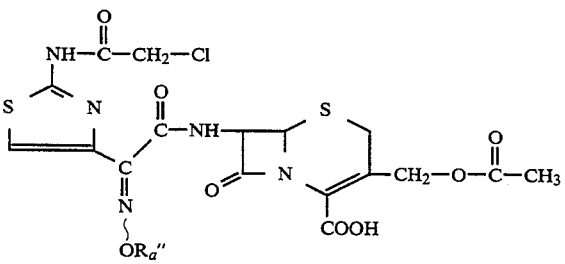

wherein $R_a''$ is selected from the group consisting of chloroacetyl, alkyl of 1 to 4 carbon atoms and alkenyl and alkynyl of 2 to 4 carbon atoms as well as compounds of the formula

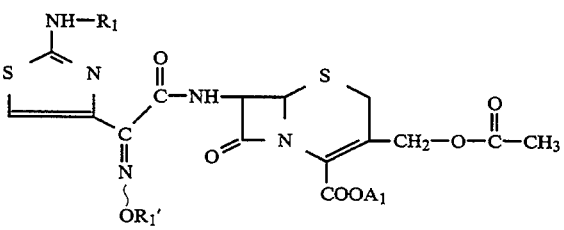

wherein $R_l$, $R_l'$ and $A_l$ have the above definitions. The latter two products also possess antibiotic properties similar to those of formula I and may be used in the same manner.

The compounds of formula III that are not known may be prepared beginning with ethyl γ-chloro-α-oximino-acetyl-acetate described in J. of Medicinal Chemistry, Vol. 16, 1973, No. 9. To obtain compounds where R' is alkyl of 1 to 4 carbon atoms or alkenyl or alkynyl of 2 to 4 carbon atoms, the said ethyl ester is reacted with the corresponding hydrocarbon halide or sulfate. To obtain compounds wherein R' is a group easily removable by acid hydrolysis or hydrogenolysis the said ester is reacted by classical reactions with functional derivatives of said groups.

The products of formula III' wherein X is bromine $R_b'$ is hydrogen may be prepared by reacting a compound of the formula

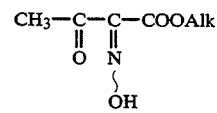

with a bromination agent under the same conditions described for the treatment of compounds of formula VII.

In addition to the compounds prepared in the specific examples, the following compounds in the syn isomer form are also part of the preferred group: 3-acetoxymethyl-7-[2-(2-amino-4-thiazolyl)-2-propyloxyiminoacetamido]-ceph-3-eme-4-carboxylic acid, 3-acetoxymethyl-7-[2-(2-amino-4-thiazolyl)-2-butyloxyiminoacetamido]-ceph-3-eme-4-carboxylic acid, 3-acetoxymethyl-7-[2-(2-amino-4-thiazolyl)-2-(2-methylpropyloxyimino)-acetamido]-ceph-3-eme-4-carboxylic acid, 3-acetoxymethyl-7-[2-(2-amino-4-thiazolyl)-2-(1,1-dimethylethoxyimino)-acetamido]-ceph-3-eme-4-carboxylic acid, 3-acetoxymethyl-7-[2-(2-amino-4-thiazolyl)-2-(2-butenyloxyimino)-acetamido]-ceph-3- eme-4-carboxylic acid, 3-acetoxymethyl-7-[2-(2-amino-4-thiazolyl)-2-(3-butenyloxyimino)-acetamido]-ceph-3-eme-4-carboxylic acid, 3-acetoxymethyl-7-[2-(2-amino-4-thiazolyl)-2-(2-butynyloxyimino)-acetamido]-ceph-3-eme-4-carboxylic acid, 3-acetoxymethyl-7-[2-(2-amino-4-thiazolyl)-2-(3-butynyloxyimino)-acetamido]-ceph-3-eme-4-carboxylic acid, 3-acetoxymethyl-7-[2-(2-amino-4-thiazolyl)-2-vinyloxyiminoacetamido]-ceph-3-eme-4-carboxylic acid, 3-acetoxymethyl-7-[2-(2-amino-4-thiazolyl)-2-(1-propenyloxyimino)-acetamido]-ceph-3-eme-4-carboxylic acid, 3-acetoxymethyl-7-[2-(2-amino-4-thiazolyl)-2-(1-propynyloxyimino)-acetamido]-ceph-3-eme-4-carboxylic acid, 3-acetoxymethyl-7-[2-(2-amino-4-thiazolyl)-2-(1-butenyloxyimino)-acetamido]-ceph-3-eme-4-carboxylic acid, 3-acetoxymethyl-7-[2-(2-amino-4-thiazolyl)-2-(1-ethynyloxyimino)-acetamido]-ceph-3-eme-4-carboxylic acid, 3-acetoxymethyl-7-[2-(2-amino-4-thiazolyl)-2-(2-propynyloxyimino)-acetamido]-ceph-3-eme-4-carboxylic acid and 3-acetoxymethyl-7-[2-(2-amino-4-thiazolyl)-2-(1-butynyloxyimino)-acetamido]-ceph-3-eme-4-carboxylic acid and their salts with alkali metals, alkaline earth metals, magnesium and organic amines.

In the following examples there are described several preferred embodiments to illustrate the invention. However, it should be understood that the invention is not intended to be limited to the specific embodiments.

EXAMPLE 1

3-acetoxymethyl-7-[2-(2-tritylamino-4-thiazolyl)-2-tritylhydroxyiminoacetamido]-ceph-3-eme-4-carboxylic acid

STEP A: Ethyl 2-(2-amino-4-thiazolyl)-2-hydroxyiminoacetate

A mixture of 2 g of ethyl $\gamma$-chloro-$\alpha$-oximinoacetylacetate, 5 ml of ethanol and 0.76 g of thiourea was stirred at room temperature for 16 hours while the hydrochloride crystallized and after dilution with 5 ml of ether, the mixture was vacuum filtered. The filter was rinsed with a 1—1 ethanol-ether mixture and then ether to obtain 1.55 g of the hydrochloride salt which was dissolved at 40°–50° C. in 8 ml of water. The solution was neutralized to a pH of 5–6 by addition of sodium acetate and the free ethyl 2-(2-amino-4-thiazolyl)-2-hydroxyiminoacetate crystallized. The mixture was iced and then was vacuum filtered and the product was washed with water and dried to obtain 1.22 g of the anti-isomer melting at 154° C.

The combined wash waters were concentrated and the residue was taken up in water. The solution was washed with ether and sodium bicarbonate was added thereto. The mixture was vacuum filtered and the product was washed with water to obtain 1.9 g of a product having two spots in thin layer chromatography. The product was chromatographed over silica gel, was eluted with ether and the combined pure fractions of the concentrated syn isomer were empasted with ether vacuum filtered and dried to obtain 50 mg of the syn isomer.

STEP B: Ethyl 2-(2-tritylamino-4-thiazolyl)-2-tritylhydroxyiminoacetate

A solution of 15 g of trityl chloride in 30 ml of chloroform was added at 10° C. to a solution of 5.4 g of the product of Step A in 54 ml of chloroform and 7.5 ml of triethylamine and after standing for an hour, the mixture was washed with 40 ml of water and then 20 ml of water containing 4 ml of N hydrochloric acid. The mixture was decanted and the organic phase was dried and evaporated to dryness. The residue was taken up in 10 ml of ether and 50 ml of methanol were added with stirring. The mixture was vacuum filtered and the product was washed with methanol to obtain in 2 crops 14.2 g of ethyl 2-(2-tritylamino-4-thiazolyl)-2-tritylhydroxyiminoacetate.

STEP C: 2-(2-tritylamino-24-thiazolyl)-2-tritylhydroxyiminoacetic acid

A suspension of 10.5 g of the ester of Step B in 55 ml of dioxane was brought to approximately reflux and 17 ml of 2N sodium hydroxide were slowly added thereto. The mixture was brought to a slight reflux and was cooled and vacuum filtered. The salt product was taken up in 60 ml of methylene chloride, 20 ml of water and 2 ml of acetic acid and the mixture was vacuum filtered. The product was washed with water to obtain a first crop of 7 g of 2-(2-tritylamino-4-thiazolyl)-2-trithylhydroxyimino-acetic acid. The dioxane was evaporated from the filtrate and 20 ml of methylene chloride, 10 ml of water and 1 ml of acetic acid were added to obtain a second crop of 1.5 g of the said acid for a total yield of 8.5 g.

Analysis: $C_{43}H_{33}O_3N_3S \cdot 0.5\ H_2O$

| | | | |
|---|---|---|---|
| Calculated: | % C 75.85 | % H 5.03 | % N 6.17 | % S 4.7 |
| Found: | 75.8 | 4.9 | 5.9 | 4.6 |

STEP D: 3-acetoxymethyl-7-[2-(2-tritylamino-4-thiazolyl)-2-tritylhydroxyiminoacetamido]-ceph-3-eme-4-carboxylic acid 5 ml of N-methyl-morpholine were added with stirring to a suspension of 8.5 g of the acid of Step C and 50 ml of methanol and after stirring the mixture for 10 minutes at 30° C., 30 ml of methylene chloride were added thereto. The mixture was concentrated and 100 ml of ether were added thereto. The mixture effloresced and was vacuum filtered. The recovered precipitate was washed with ether and dried to obtain a first crop of 7.2 g of the N-methyl-morphine salt. The filtrate was evaporated to dryness and the residue was taken up in ether to obtain a second crop of the same salt.

A suspension of 4.24 g of the salt in 60 ml of methylene chloride was stirred under an inert gas for 5 minutes and after cooling to $-5°$ C., 6 ml of a molar solution of isobutyl chloroformate in methylene chloride were added thereto. The mixture was stirred at $-5°$ C. for 15 minutes and was then cooled to $-20°$ C. after which a solution of 1.36 g of 7-amino-cephalosporanic acid in 25 ml of methylene chloride and 1.4 ml of triethylamine was added. The mixture stood for an hour at room temperature and was washed with 50 ml of water containing 10 ml of N-hydrochloric acid and was vacuum filtered. The filtrate was decanted and the organic phase was washed with water and evaporated to dryness. The residue was triturated with ether, vacuum filtered and washed with ether to obtain 4.5 g of raw product. The raw product in 10 ml of methylene chloride was stirred for an hour at 10° C. and was vacuum filtered. The filter was rinsed with methylene chloride and 50 ml of ether were added to the filtrate. The mixture was stirred and vacuum filtered and the precipitate was washed with ether to obtain 2.29 g of 3-acetoxymethyl-7-[2-(2-tritylamino-4-thiazolyl)-2-tritylhydroxyiminoacetamido]-ceph-3-eme-4-carboxylic acid. A second crop of 0.856 g of the said product was also obtained for a total yield of 3.146 g.

EXAMPLE 2

3-acetoxymethyl-7-[2-(2-amino-4-thiazolyl)-2-hydroxyiminoacetamido]-ceph-3-eme-4-carboxylic acid A suspension of 2.29 g of the acid of Example 1 in 18.4 ml of 50% aqueous formic acid was stirred at 55° C. for 15 minutes and was then cooled. 10 ml of water were added thereto and the mixture was vacuum filtered. The filtrate was washed with water and concentrated to dryness under reduced pressure. The residue was added to acetone and the mixture was vacuum filtered. 30 ml of ether were added to the filtrate and the mixture was stirred and vacuum filtered. The recovered product was washed with ether to obtain 0.665 g of 3-acetoxymethyl-7-[2-(2-amino-4-thiazolyl)-2-hydroxyiminoacetamido]-ceph-3-eme-4-carboxylic acid. A second crop of 0.123 g of the product was obtained by crystallization for a total yield of 0.788 g. 70 mg of carbon black were added to a solution of 0.735 g of the said product in 7.5 ml of ethanol and 7.5 ml of acetone and the mixture was vacuum filtered. The filtrate was evaporated to dryness and the residue was effloresced with ethanol and washed with ethanol to obtain a first yield of 0.450 g and a second yield of 0.105 g of 3-acetoxymethyl-7-[2-(2-amino-4-thiazolyl)-2-hydroxyiminoacetamido]-ceph-3-eme-4-carboxylic acid.

Infrared Spectrum: Carbonyl at 1774, 1740 and 1676$^{cm-1}$; —C=C—NH$_2$ at 1630$^{cm-1}$ and NH at 1520$^{cm-1}$.

EXAMPLE 3

3-acetoxymethyl-7-[2-(2-tritylamino-4-thiazolyl)-2-methoxyiminoacetamido]-ceph-3-eme-4-carboxylic acid

STEP A: ethyl 2-(2-amino-4-thiazolyl)-2-methoxyiminoacetate

A mixture of 22.5 g of ethyl γ-chloro-α-oximino acetylacetate in 100 ml of methylene chloride was placed in an ice bath and 275 ml of a fresh solution of diazomethane (21.6 g/l) in methylene chloride were slowly added with stirring. The mixture was allowed to stand for 5 minutes and then excess diazomethane was destroyed with a little alumina. The mixture was concentrated to dryness and the residue was chromatographed over silica gel and was eluted with methylene chloride to obtain 11.93 g of ethyl γ-chloro-α-methoxyimino-acetylacetate.

A mixture of 1 g of ethyl γ-chloro-α-methoxyiminoacetylacetate, 3 ml of absolute ethanol and 0.42 g of powdered thiourea was stirred at room temperature for about 2 hours and was then diluted with 60 ml of ether which caused the hydrochloride to crystallize. The mixture was stirred and vacuum filtered and the recovered precipitate was washed and dried to obtain 685 mg of the hydrochloride of ethyl 2-(2-amino-4-thiazolyl)-2-methoxyiminoacetate. The latter was dissolved in 4 ml of water at 50° C. and potassium acetate was added until the solution had a pH of 6 at which the free amine crystallized. The mixture was cooled and vacuum filtered and the recovered precipitate was washed with water and dried to obtain 270 mg of ethyl 2-(2-amino-4-thiazolyl)-2-methoxyiminoacetate melting at 161° C. and having a syn configuration. RMN spectrum (CDCl$_3$ 60 MHZ) ppm: 4-(NOCH$_3$), 6.7 (proton of thiazolic ring).

STEP B: Ethyl 2-(2-tritylamino-4-thiazolyl)-2-methoxyiminoacetate 2.9 ml of triethylamine were added at −10° C. to a mixture of 4.6 g of the product of Step A in 92 ml of methylene chloride and after cooling to −35° C., 6.1 g of trityl chloride were added thereto. The temperature was allowed to rise to room temperature in about 2½ hours and the reaction mixture was washed with water and then with 0.5N hydrochloric acid and finally with aqueous sodium acetate. The mixture was dried and evaporated to dryness. The residue was taken up in ether and the solution was concentrated to dryness again. The residue was dissolved in methanol and water and ether were added to cause crystallization. The mixture was vacuum filtered and the recovered precipitate was washed with ether to obtain 6.15 g of ethyl 2-(2-tritylamino-4-thiazolyl)-2-methoxyiminoacetate melting at 120° C. having the syn configuration.

STEP C: 2-(2-tritylamino-4-thiazolyl)-2-methoxyiminoacetic acid

A solution of 7.01 g of the ester of Step B in 35 ml of dioxane was heated to 110° C. on an oil bath and 9 ml of 2N sodium hydroxide solution was added thereto over 5 minutes. The mixture was stirred at reflux for 30 minutes and the sodium salt crystallized. The mixture was cooled and vacuum filtered and the recovered precipitate was washed with dioxane and then with ether to obtain a first crop of 5.767 g of a salt. The filtrate was concentrated to obtain a second crop of 1.017 g of sodium salt for a total yield of 6.784 g. 3.06 g of the said salt were dissolved in 65 ml of methylene chloride and 6.5 ml of 2N hydrochloric acid and the solution was washed with water, dried and evaporated to dryness to obtain a quantitative yield of 2-(2-tritylamino-4-thiazolyl)-2-methoxyiminoacetic acid with a syn configuration.

RMN (DMSO, 60 MHZ) ppm: 3.68 (N—OCH$_3$), 6.6 (proton of thiazolic ring).

STEP D: 3-acetoxymethyl-7-[2-(2-tritylamino-4-thiazolyl)-2-methoxyiminoacetamido]-ceph-3-eme-4-carboxylic acid.

0.78 g of dicyclohexylcarbodiimide was added to a solution of the dry acid of Step C in 30 ml of dry methylene chloride and the mixture was stirred for an hour at room temperature and was then vacuum filtered to remove dicyclohexyl urea formed. The filtrate was cooled to −10° C. and a solution of 1.01 g of 7-aminocephalosporanic acid in 13 ml of methylene chloride and 0.9 ml of triethylamine was added. The temperature returned to room temperature and 1 ml of acetic acid was added thereto. The mixture was vacuum filtered and the filtrate was washed with aqueous hydrochloric acid, dried and concentrated to dryness. The residue was taken up in 10 ml of dioxane and 1 ml of water and 3 ml of a saturated sodium bicarbonate aqueous solution were added thereto. The mixture was stirred and vacuum filtered and the filtrate was washed and evaporated to dryness. The residue was taken up in methylene chloride and the solution was washed with 10 ml of water and 5 ml of N hydrochloric acid. The mixture was decanted and the organic phase was washed with water, dried and effloresced with ether to obtain 1.747 g of raw product. The latter was dissolved in ethyl acetate and was crystallized by addition of ether to obtain 1.255 g of pure 3-acetoxymethyl-7-[2-(2-tritylamino-4-thiazolyl)-2-methoxyiminoacetamido]-ceph-3-eme-4-carboxylic acid in the syn configuration.

EXAMPLE 3A

Ethyl 2-(2-amino-4-thiazolyl)-2-methoxyiminoacetate

STEP A': Ethyl 2-acetyl-2-methoxyiminoacetate 234 g of potassium carbonate were added at 10° C. under a nitrogen atmosphere to a mixture of 180 g of raw ethyl 2-acetyl-2-hydroxyiminoacetate in 900 ml of pure acetone and then 103 ml of dimethyl sulfate were added thereto. The mixture was stirred at room temperature for 3 hours and was then poured into ice and 4 liters of water were added. The mixture was extracted with methylene chloride and the extracts were washed with water, dried and distilled to dryness to obtain 185 g of ethyl 2-acetyl-2-methoxyiminoacetate.

STEP B': Ethyl 4-bromo-2-methoxyiminoacetylacetate 200 mg of p-toluene sulfonic acid were added to a mixture of 197 g of the product of Step A' in 1 liter of methylene chloride and then 0.1M of a solution of 191 g of bromine in 200 ml methylene chloride were added thereto at 20° C. When the reaction had started, the rest of the bromine solution was added over an hour at 20° C. The temperature was raised to 25° C. at the end of the reaction and the mixture was washed with ice water and extracted with methylene chloride. The organic extracts were dried and distilled to dryness to obtain 268 g of ethyl 4-bromo-2-methoxyiminoacetylacetate.

STEP C': Ethyl 2-(2-amino-4-thiazolyl)-2-methoxyiminoacetate

A solution of 268 g of the product of Step B' in 270 ml of ethanol was added under a nitrogen atmosphere over 30 minutes to a solution of 80 g of thiourea, 270 ml of ethanol and 540 ml of water and the mixture was stirred for an hour at 20° C. The mixture was cooled to 15° C. and small amounts of potassium bicarbonate were added to obtain a pH of 5. The mixture was vacuum filtered and the recovered product was washed with water and dried to obtain 133.8 g of ethyl 2-(2-amino-4-thiazolyl)-2-methoxyiminoacetate which was identical to the product obtained in Step A of Example 3.

EXAMPLE 4

3-acetoxymethyl-7-[2-(2-amino-4-thiazolyl)-2-methoxyiminoacetamido]-ceph-3-eme-4-carboxylic acid A mixture of 0.975 g of the product of Example 3 in 4 ml of 50% aqueous formic acid was stirred at 55° C. for 10 minutes and 4 ml of water were added thereto. The mixture was vacuum filtered and the filtrate was evaporated to dryness under reduced pressure. The residue was effloresced with 2 ml of ethanol and was vacuum filtered. The product was washed with ethanol and then with ether to obtain 0.428 g of pure 3-acetoxymethyl-7-[2-(2-amino-4-thiazolyl)-2-methoxyiminoacetamido]-ceph-3-eme-4-carboxylic acid with a syn configuration.

RMN (DMSO 60 MHZ) ppm: 2.03

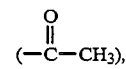

doublet 9.58 J=8 HZ (CONH), 6.76 (proton of thiazolic ring).

Analysis: $C_{16}H_{17}O_7N_5S_2$

| | % C | % H | % N | % S |
|---|---|---|---|---|
| Calculated: | 42.19 | 3.76 | 15.37 | 14.08 |
| Found: | 42.3 | 4.1 | 15.2 | 13.8 |

EXAMPLE 5

Diethylamine salt of 3-acetoxymethyl-7-[2-(2-tritylamino-4-thiazolyl)-2-methoxyiminoacetamido]-ceph-3-eme-4-carboxylic acid The raw acid of Example 3 formed by condensation of 40.8 g of 7-amino-cephalosporanic acid and the anhydride of dicyclohexylcarbodiimide and 2-(2-tritylamino-4-thiazolyl)-2-methoxyimino-acetic acid reaction was dissolved in 350 ml of dioxane and 350 ml of ether and then 33 ml of diethylamine were slowly added thereto with stirring. The mixture was stirred for 20 minutes and the precipitated product was recovered by vacuum filtration, was washed twice with the above ether-dioxane mixture to obtain 62.6 g of product. The filtrate was concentrated to a syrupy consistency and was then added to 2.0 liters of ether. The mixture was stirred and vacuum filtered to obtain 110.3 g of the diethylamine salt of 3-acetoxymethyl 7-[2-(2-tritylamino-4-thiazolyl)-2-methoxyiminoacetamido]-ceph-3-eme-4-carboxylic acid in the syn configuration.

EXAMPLE 6

3-acetoxymethyl-7-[2-(2-amino-4-thiazolyl)-2-methoxyiminoacetamido]-ceph-3-eme-4-carboxylic acid A mixture of 36 g of the product of Example 5 and 180 ml of 50% aqueous formic acid was stirred at 50° C. for 20 minutes and the triphenyl carbinol formed was removed by vacuum filtration. 180 ml of ethanol were added to the filtrate and the mixture was evaporated to dryness under reduced pressure. The residue was taken up in a mixture of 100 ml of water and 20 ml of ethanol and was evaporated to dryness again. The residue was taken up in 100 ml of water and the mixture was stirred for 15 minutes and was vacuum filtered. The recovered product was washed with water and then ether to obtain 15.6 g of 3-acetoxymethyl-7-[2-(2-amino-4-thiazolyl)-2-methoxyiminoacetamido]-ceph-3-eme-4-carboxylic acid which was identical to the product of Example 4.

EXAMPLE 7

Sodium 3-acetoxymethyl-7-[2-(2-amino-4-thiazolyl)-2-methoxyiminoacetamido]-ceph-3-eme-4-carboxylate A solution of 8 g of sodium bicarbonate in about 20 ml of ethanol was progressively added to 45.55 g of pure 3-acetoxymethyl-7-[2-(2-amino-4-thiazolyl)-2-methoxyiminoacetamido]-ceph-3-eme-4-carboxylic acid of Example 4 in 100 ml of distilled water and another 80 ml of ethanol and 4.5 g of activated carbon were added thereto. The mixture was stirred for 5 minutes and was filtered. The filter was rinsed with ethanol and the filtrate was evaporated to dryness under reduced pressure. The residue was taken up in 100 ml of ethanol and evaporated to dryness again. The residue was dissolved in 100 ml of methanol and the solution was poured into 2 liters of acetone. The mixture was vigorously stirred and was vacuum filtered. The recovered product was rinsed with acetone and then ether and dried under reduced pressure to obtain 43.7 g of a white product which rehydrated in air to obtain a final weight of 45.2 g of sodium 3-acetoxymethyl-7-[2-(2-amino-4-thiazolyl)-2-methoxyiminoacetamido]-ceph-3-eme-4-carboxylate with a specific rotation $[\alpha]_D^{20} = +55° \pm 2°$ (C=0.8% in water). The product had a syn configuration.

RMN (D$_2$O-60 MHZ) ppm: 2.01 (COCH$_3$), doublet at 9.53 J=8 HZ (NHCO), 6.75 (proton of thiazolic ring).

| Analysis: | | | | | | | | | |
|---|---|---|---|---|---|---|---|---|---|
| Calculated: | % | 40.24 | % | 3.38 | % | 14.67 | % | 13.43 | % 4.81 |
| | C | | H | | N | | S | | Na |
| Found: | | 40.3 | | 3.8 | | 14.4 | | 13.3 | 4.84 |

EXAMPLE 8

3-acetoxymethyl-7-[2-(2-tritylamino-4-thiazolyl)-2-(2-propenyl)oxyiminoacetamido]-ceph-3-eme-4-carboxylic acid

STEP A: Ethyl 2-(2-amino-4-thiazolyl)-2-(2-propenyl)oxyiminoacetate 27.5 ml of 2N sodium hydroxide solution was added to an ice-cooled mixture of 9.7 g of ethyl 2-hydroxyimino-4-chloro-acetylacetate, 30 ml of acetone and 9.15 ml of 3-iodopropene and the mixture stood for 1½ hours at room temperature. 3.8 g of thiourea were added to the reaction mixture and the mixture was then heated at 60° C. for 15 minutes and stood at room temperature for 45 minutes. The acetone was then evaporated and methylene chloride, water and potassium carbonate were added thereto. The mixture was stirred and decanted. The aqueous phase was extracted with methylene chloride and the organic extracts were dried and evaporated to dryness to obtain 9.75 g of residue. The latter was chromatographed over silica gel and was eluted with ether to obtain 2.7 g of product. The latter was taken up in isopropyl ether and the mixture was vacuum filtered. The recovered crystals were rinsed and dried to obtain 783 mg of ethyl 2-(2-amino-4-thiazolyl)-2-(2-propenyl)-oxyiminoacetate melting at 100° C. and having the syn configuration.

STEP B: Ethyl 2-(2-tritylamino-4-thiazolyl)-2-(2-propenyl)oxyiminoacetate 615 mg of trityl chloride were added at −15° C. to a mixture of 511 mg of the product of Step A, 0.9 ml of dimethylformamide, 1.8 ml of methylene chloride and 0.29 ml of triethylamine and the mixture stood for 1½ hours at room temperature. 2 ml of 1N hydrochloric acid and then 5 ml of water were added thereto and the mixture was decanted. The organic solution was dried and concentrated to dryness to obtain 1.28 g of raw ethyl 2-(2-tritylamino-4-thiazolyl-2-(2-propenyl)oxyiminoacetate with a syn configurate.

STEP C: 2-(2-tritylamino-4-thiazolyl)-2-(2-propenyl)oxyiminoacetic acid

A mixture of 1.28 g of the product of Step B, 6.2 ml of dioxane and 3 ml of 2N sodium hydroxide solution was formed at 120° and was refluxed for an hour during which a sodium salt crystallized. The mixture was vacuum filtered and the recovered product was rinsed with a dioxane-ether mixture and dried to obtain 805 mg of the sodium salt. The latter was added to 10 ml of methylene chloride and 3 ml of 1N hydrochloric acid and the mixture was stirred until dissolution occurred. The mixture was decanted and the organic phase was dried and concentrated to dryness. The residue was taken up in ether and the mixture was vacuum filtered to obtain 715 mg of 2-(2-tritylamino-H-thiazolyl)-2-(2-propenyl-)oxyiminiacetic acid with a melting point of 170° C. and a syn configuration.

STEP D: 3-acetoxymethyl-7-[2-(2-tritylamino-4-thiazolyl)-2-(2-propenyl)oxyiminoacetamido]-ceph-3-eme-4-carboxylic acid A mixture of 470 mg of the product of Step C, 5 ml of methylene chloride and 130 ml of dicyclohexylcarbodiimide was rinsed with a little methylene chloride and the mixture was stirred for an hour at room temperature. The mixture was vacuum filtered to remove the dicyclohexylurea formed and the filtrate was cooled. A solution of 136 mg of 7-amino-cephalicsporanic acid, 2.4 ml of methylene chloride and 0.14 ml of triethylamine was added to the filtrate under an inert atmosphere and the mixture sat for 1½ hours at room temperature 2 ml of 1N hydrochloric acid and water were added thereto and the mixture was stirred and decanted. The organic phase was washed with water, dried and evaporated to dryness to obtain 610 mg of raw 3-acetoxymethyl-7-[2-(2-tritrylamino-4-thiazolyl-2-(2-propenyl) oxyiminoacetamido]-ceph-3-eme-4-carboxylic acid with a syn configuration.

EXAMPLE 9

3-acetoxymethyl-7-[2-(2-amino-4-thiazolyl)-2-(2-propenyl)oxyiminoacetamido]-ceph-3-eme-4-carboxylic acid A mixture of 610 mg of the product of Example 8 and 3 ml of 50% aqueous formic acid was heated at 60° C. for 15 minutes and 4 ml of water were added. The mixture was stirred and vacuum filtered. The filtrate was rinsed with water and concentrated to dryness under reduced pressure. The residue was taken up in water and was effloresced. The mixture was vacuum filtered and the product was rinsed to obtain 120 mg of 3-acetoxymethyl-7-[2-(2-amino-4-thiazolyl)-2-(2-propenyl) oxyiminoacetamido]-ceph-3-eme-4-carboxylic acid with a melting point of about 160° C. and a syn configuration.

U.V. Spectra (ethanol): Max. at 236 nm: $E_1^1$=375; $\epsilon$=18,000. Inflex. towards 252 nm: $E_1^1$=316. Inflex. towards 295 nm: $E_1^1$=138; $\epsilon$=6,600.

U.V. Spectrum (ethanol —0.1N HCl): Max. at 263 nm: $E_1^1$=380; $\epsilon$=18,300. Inflex. towards 280 nm: $E_1^1$=317.

RMN (DMSO-90 MHZ) ppm: 2.02 (OAc), 6.68 (proton of thiazolic ring).

EXAMPLE 10

3-acetoxymethyl-7-[2-(2-tritylamino-4-thiazolyl)-2-ethoxyiminoacetamido]-ceph-3-eme-4-carboxylic acid

STEP A: Ethyl 2-(2-amino-4-thiazolyl)-2-ethoxyiminoacetate 53 ml of 2N sodium hydroxide solution were added over 30 minutes to a mixture of 19.4 g of ethyl γ-chloro-α-oxyiminoacetoacetate in 60 ml of acetone and 14.3 ml of diethyl sulfate which had set in an ice bath for 10 minutes and the mixture was stirred for 40 minutes. 7.6 g of thiourea were added to the reaction mixture which was then heated to 55° C. for 20 minutes and the acetone was evaporated. The residue was taken up in ethyl acetate and after adding 6.9 g of potassium carbonate thereto, the mixture was stirred and decanted. The mixture was extracted with ethyl acetate and the extracts were dried and evaporated to dryness. The 17.4 of residue were chromatographed over silica gel and were eluted with ether. The product was taken up in isopropyl ether and was vacuum filtered. The recovered product was rinsed and dried to obtain 2.8 g of ethyl 2-(2-amino-4-thiazolyl)-2-ethoxyiminoacetate melting at 129° C. and having the syn configuration.

STEP B: Ethyl 2-(2-tritylamino-4-thiazolyl)-2-ethoxyiminoacetate 3.98 g of trityl chloride were slowly added under an inert atmosphere to a mixture of 3.16 g of the product of Step A, 6 ml of dimethylformamide, 12 ml of methylene chloride and 1.89 ml of triethylamine cooled to −15° C. and the mixture stood at 10° C. for 30 minutes and then 3 hours at room temperature. 13 ml of N hydrochloric acid were added to the mixture which was stirred and decanted. The organic phase was washed with N hydrochloric acid, then with water and was extracted with methylene chloride. The extracts were dried and evaporated to dryness to obtain 7.89 g of raw ethyl 2-(2-tritylamino-4-thiazolyl)-2-ethoxyiminoacetate having a syn configuration.

STEP C: 2-(2-tritylamino-4-thiazolyl)-2-ethoxyimino-acetic acid

A mixture of 7.89 g of the product of Step B, 40 ml of dioxane and 19.5 ml of 2N sodium hydroxide was heated for one hour at 110° C. and was vacuum filtered. The recovered product was rinsed with a mixture of ether and dioxane and then with ether and dried to obtain 6.25 g of a sodium salt. The latter was taken up in 60 ml of methylene chloride and 20 ml of N hydrochloric acid and the two phases were stirred, 20 ml of methanol were added thereto and the mixture was decanted. The organic phase was washed with water and was extracted with a methylene chloride-methane mixture. The extracts were dried and evaporated to dryness to obtain 5.85 g of pure 2-(2-tritylamino-4-thiazolyl)-2-ethoxyimino-acetic acid with a syn configuration.

STEP D: 3-acetoxymethyl-7-[2-(2-tritylamino-4-thiazolyl)--2ethoxyiminoacetamido]-ceph-3-eme-4-carboxylic acid 970 mg of dicyclohexylcarbodiimide were added to a cooled suspension of 3.43 g of the acid of Step C in 34 ml of methylene chloride and the mixture was rinsed with methylene chloride and was stirred for an hour at room temperature. The mixture was vacuum filtered and the filtrate was cooled to −20° C. and was poured all at once into a solution of 1.02 g of 7-amino-cephalosporanic acid in 18 ml of methylene chloride and 1.06 ml of triethylamine cooled to −20° C. The mixture was reheated for 1½ hours and 1.8 ml of acetic acid were added thereto. 9 ml of N hydrochloric acid were added and the mixture was stirred and decanted. The organic phase was washed with water and was extracted methylene chloride. The extracts were dried and evaporated to obtain 4.56 g of 3-acetoxymethyl-7-[2-(2-tritylamino-4-thiazolyl)-2-ethoxyiminoacetamido]-ceph-3-eme-4-carboxylic acid with a syn configuration.

EXAMPLE 11

3-acetoxymethyl-7-[2-(2-amino-4-thiazolyl)-2-ethoxyiminoacetamido]-ceph-3-eme-4-carboxylic acid A mixture of 4.56 g of the product of Example 10 and 23 ml of 50% aqueous formic acid was heated at 55° C. for 15 minutes and was then diluted with 30 ml of water. The mixture was vacuum filtered and the filtrate was evaporated to dryness. The residue was taken up in water and the mixture was stirred and vacuum filtered. The recovered product was rinsed and dried to obtain 116 mg of impure product. The filtrate was concentrated to obtain a second crop of 674 mg of product for a total yield of 790 mg.

The 1.063 g of raw product was empasted with 5 ml of water and the mixture was heated at 70° C. for 5 minutes and was cooled. The mixture was stirred for 30 minutes and was vacuum filtered. The product was rinsed and dried to obtain 8.15 mg of product which was taken up in 2 ml of water and 3 ml of acetone. The mixture was slowly heated and was vacuum filtered. 3 ml of water were added to the filtrate and the mixture was heated to 60° C. and the acetone was removed by bubbling nitrogen therethrough. The mixture was vacuum filtered and the recovered product was rinsed with water, then with ether to obtain 438 mg of 3-acetoxymethyl-7-[2-(2-amino-4-thiazolyl)-2-ethoxyiminoacetamido]-ceph-3-eme-4-carboxylic acid with syn configuration.

Analysis: $C_{17}H_{19}O_7N_5S_2$

| | | | | |
|---|---|---|---|---|
| Calculated: | % C 43.49 | % H 4.08 | % N 14.92 | % S 13.66 |
| Found: | 44.5 | 4.4 | 14.8 | 13.3 |

RMN (60 MHZ DMSO) ppm: 2.05 (OAc), 6.75 (proton of thiazol ring).

EXAMPLE 12

3-acetoxymethyl-7-[2-(2-tritylamino-4-thiazolyl)-2-(1-methylethoxyimino)acetamido]ceph-3-eme-4-carboxylic acid

STEP A: Ethyl 2-acetyl-2-(1-methyl ethoxyimino)acetate 52 g of potassium carbonate were added to a mixture of 397.8 g of ethyl 2-acetyl-2-hydroxyiminoacetate in 200 ml of pure acetone cooled on an ice bath and then 25 ml of 2-iodopropane were added thereto over 25 minutes. The mixture was stirred for 2 hours and 800 ml of water and 500 of methylene chloride were added thereto. The mixture was stirred and decanted and the aqueous phase was extracted with methylene chloride. The mixture was dried and vacuum filtered and the filtrate was evaporated to obtain 41.5 g of ethyl 2-acetyl-2-(1-methylethoxyimino)-acetate.

STEP B: Ethyl 4-bromo-2-(1-methylethoxyimino)-acetylacetate

A mixture of 41.5 g of the product of Step A in 190 ml of methylene chloride with traces of p-toluene sulfonic acid was stirred and a solution of 11.9 ml of bromine in 50 ml of methylene chloride was added thereto over an hour at room temperature. The mixture was stirred and was then poured into ice water and was decanted. The aqueous phase was extracted with methylene chloride and the extracts were washed with ice water, dried and evaporated to dryness to obtain 55 g of ethyl-4-bromo-2-(1-methylethoxyimino)-acetylacetate.

STEP C: Ethyl 2-(2-amino-4-thiazolyl)-2-(1-methylethoxyimino)-acetylacetate

A solution of 55 g of the product of Step B in 55 ml of ethanol was added over 40 minutes to a solution of 14.9 g of thiourea in 55 ml of ethanol and 105 ml of water and the mixture was stirred at room temperature for 2½ hours. 220 ml of 10% sodium bicarbonate in water was added thereto and the mixture was stirred and vacuum filtered. The recovered product was rinsed and dried to obtain 42.15 g of raw product. The latter was subjected to chromatography with elution with ether. The fractions rich in the desired product were combined and evaporated to dryness. The residue was taken up in isopropyl ether and the mixture was vacuum filtered. The recovered product was rinsed to obtain 10.75 of ethyl 2-(2-amino-4-thiazolyl)-2-(1-methylethoxyimino)acetate in the syn configuration.

STEP D: Ethyl 2-(2-tritlyamino-4-thiazolyl)-2-(1-methylathoxyimino)-acetate 13.2 g of trityl chloride were slowly added to a cooled mixture of 11 g of the product of Step C, 20 ml of dr dimethylformamide, 40 ml of methylene chloride and 6.2 ml of triethylamine and the mixture was stirred for 2½ hours. 43 ml of N hydrochloric acid were added thereto and the mixture was stirred and decanted. The organic phase was washed with 40 ml of water and was extracted with methylene chloride The extracts were dried and vacuum filtered. The filtrate was evaporated to dryness to obtain 27.7 g of ethyl 2-(2-tritylamino-4-thiazolyl)-2-(1-methylethoxyimino)-acetate in the syn configuration.

STEP E: 2-(2-tritylamino-4-thiazolyl)-2-(1-methylethoxyimio)-acetate acid

A mixture of 27.7 g of the product of Step D, 150 ml of dioxane and 65 ml of 2N sodium hydroxide was refluxed for 2 hours and the mixture was cooled for crystallization of a sodium salt. The mixture was vacuum filtered and the recoved product was rinsed with a 1-1 ether-dioxane mixture and dried to obtain 16.85 g of raw sodium 2-(2-tritylamino-4-thiazolyl)-2-(1-methylethoxyimino)-acetate.

15.9 g of the said salt were dissolved in 15.9 g of dimethylformamide, 100 ml of water and 500 ml of methanol and 30 ml of 2N hydrochloric acid were added thereto. The methanol was evaporated and the mixture was diluted with water and was vacuum filtered. The recovered precipitate was rinsed and dried to obtain 9.8 g of viscous product which was taken up in 220 ml of a 1—1 methylene chloride-methanol mixture. The mixture was evaporated to dryness and the residue was taken up in ether. After efflorescence, the mixture was vacuum filtered and the recovered product was rinsed with methylene chloride and with water and dried to obtain 4.9 mg of 2-(2-tritylamino-4-thiazolyl)-2-(1-methylethoxyimino)acetic acid in the syn configuration and melting at 170° C. For analysis, 300 mg of the product were dissolved in 2 ml of methylene chloride and 1 ml of ethanol and the solution was diluted with water and methylene chloride. The mixture was stirred and vacuum filtered and the recovered crystals were rinsed with methylene chloride and water dried to obtain 230 mg of product for analysis.

| Analysis: | | | | |
|---|---|---|---|---|
| Calculated: | % C 68.77 | % H 5.34 | % N 8.91 | % S 6.8 |
| Found: | 68.6 | 5.5 | 8.8 | 6.8 |

STEP F: 3-acetoxymethyl-7-[2-(2-tritylamino-4-thiazolyl)-2-(1-methylethoxyimino)-acetamido]-ceph-3-eme-4-carboxylic acid A solution of 1.62 g of dicyclohexylcarbodiimide in 16 ml of methylene chloride was added under an inert atmosphere to a solution of 4.89 g of the product of Step D in 13.5 ml of dimethylformamide in an ice bath and the mixture was stirred in the ice bath and then vacuum filtered. The recovered product was rinsed with methylene chloride and dried to remove 1.424 g of dicyclohexylurea. The filtrate was cooled in a methanol-ice bath and a solution of 1.41 g of 7-aminocephalosporanic acid in 30 ml of methylene chloride and 1.45 ml of triethylamine were added thereto. The mixture was stirred for 3 hours at room temperature and after the addition of 20 ml of N hydrochloric acid, the mixture was stirred and decanted The aqueous phase was extracted with methylene chloride and the extracts were dried and vacuum filtered to obtain 9.05 g of a mixture of the starting material and final product. The mixture was taken up in methylene chloride and was seeded Crystallization was effected with stirring and the mixture was vacuum filtered. The crystals were rinsed and dried to obtain 1.6 g of pure starting material. The filtrate was evaporated to dryness and the residue was taken up in isopropyl ether with vigorous stirring to obtain 4.91 g of insoluble viscous 3-acetoxymethyl-7-[2-(2-tritylamino-4-thiazoly-2-(1-methylethoxyimino)-acetamido]-ceph-3-4-carboxylic acid in the syn configuration.

EXAMPLE 13

3-acetoxymethyl-7-[2-(2-amino-4-thiazolyl)-2-(1-methylethoxyimino)-acetamido]-ceph-3eme-4-carboxylic acid A mixture of 4.91 g of raw product of Example 12 in 30 ml of 50% aqueous formic acid was stirred in a water bath at 60° C. and was then diluted with water and vacuum filtered. The filter was rinsed with water and the product was dried to obtain 1.39 g of triphenylcarbinol. The filtrate was evaporated to dryness and the residue was taken up in water and effloresced. The mixture was vacuum filtered and the recovered product was rinsed with water and dried to obtain 800 mg of 3-acetoxymethyl-7-[2-(2-amino-4-thiazolyl)-2-(1-methylethoxyimino)-acetamido]-ceph-3-eme-4-carboxylic acid. 972 mg of the product were dissolved in 4 ml of methanol and the solution was diluted with 20 ml of ether and vacuum filtered. The product was rinsed and dried to obtain 404 mg of the said acid for analysis in the syn configuration and melting at ≈200° C.

Analysis:

| Calculated: | % C 44.71 | % H 4.38 | % N 14.48 | % S 13.26 |
|---|---|---|---|---|
| Found: | 44.5 | 4.5 | 14.1 | 13.2 |

RMN spectra (60 MHZ DMSO) ppm: 2.01 (CH$_3$CO); doublet at 9.46 J=8 HZ (CONH); 6.7 (proton of thiazole ring).

EXAMPLE 14

3-acetoxymethyl-7-[2-(2-tritylamino-4-thiazolyl)-2-ethoxyimino)acetamido]-ceph-3-eme-4-carboxylic acid

STEP A: Anti isomer of ethyl 2-(2-tritylamino-4-thiazolyl)-2-hydroxyiminoacetate 47.6 g of trityl chloride were added in small portions over 30 minutes to a mixture (cooled at −30° C.) of 32.2 g of the anti isomer of ethyl 2-(2-amino-4-thiazolyl)-2-hydroxyiminoacetate of Step A of Example 1, 90 ml of dry dimethylforamide and 24 ml of triethylamine and the mixture was left to spontaneous heating for 2½ hours. Then, 150 ml of 2N hydrochloric acid and 600 ml of water were added thereto and the mixture was stirred for 15 minutes, then vacuum filtered. The recovered precipitate was empasted 3 times with ether and was then taken up in a mixture of methanol, water and triethylamine. The mixture was stirred and then vacuum filtered. The recovered product was rinsed with aqueous methanol and dried to obtain 60.2 g of the anti isomer of ethyl 2-(2-tritylamino-4-thiazolyl)-2-hydroxyiminoacetate. 3.4 g of the said product were recrystallized from a methylene chloride-methanol mixture to obtain 3 g of pure product melting at 260° C.

STEP B: Anti isomer of ethyl 2-(2-tritylamino-4-thiazolyl)-2-ethoxyiminoacetate 16.7 ml of ethyl sulfate were added to a mixture of 11.5 g of the product of Step A, 5.85 g of potassium carbonate and 25 ml of dry dimethylformamide cooled to 15° C. and the mixture stood at room temperature for 4 hours. 420 ml of water and 250 ml of ethyl acetate were added thereto and then was stirred and decanted. The organic phase was washed with water and extracted with ethyl acetate. The extracts were dried and vacuum filtered and evaporated to dryness. The residue was taken up in ethanol and crystallization was effected. The solid product was rinsed with ethanol, empasted with petroleum ether and dried to obtain 6.6 g of the anti isomer of ethyl 2-(2-tritylamino-4-thiazolyl)-2-ethoxyiminoacetate melting at 165° C. 797 mg of product were dissolved in a 50-50 methylene chloride-ethanol mixture and the mixture was vacuum filtered. The methylene chloride was evaporated from the filtrate and the product which crystallized was recovered by vacuum filtration was rinsed with ethanol and dried to obtain 596 g of pure product.

STEP C: Anti isomer of 2-(2-tritylamino-4-thiazolyl)-2-ethoxyimino-acetic acid A mixture of 7.29 g of the product of Step B in 45 ml of dioxane and 9 ml of 2N sodium hydroxide was heated on a water bath to 50° C. for 110 minutes with stirring and was then crystallization was induced in iced water and the mixture was vacuum filtered. The recovered product was rinsed with ether to obtain 4.2 g of the sodium salt which was dissolved in 50 ml of methylene chloride, 40 ml of water and 11 ml of N hydrochloric acid. The mixture was stirred and decanted. The mixture was extracted with methylene chloride and the extracts were washed with water, dried, vacuum filtered and concentrated to dryness. The residue was taken up in 50 ml of ether and the solution was stirred and vacuum filtered. The recovered crystals were rinsed with ether to obtain 3.27 g of the anti isomer of 2-(2-tritylamino-4-thiazolyl)-2-ethoxyimino-acetic acid melting at about 200° C. with decomposition.

RMN Spectrum (60 MHZ CDCl$_3$) ppm: 7.66 (proton of thiazole ring), 7.36 (protons of trityl).

STEP D: Anti isomer of 3-acetoxymethyl-7-[2-(2-tritylamino-4-thiazolyl)-2-ethoxyimino)acetamido]-ceph-3-eme-4-carboxylic acid 1.17 ml of isobutyl chloroformate was added dropwise under an inert atmosphere to a mixture of 4.1 g of the product of Step C, 36 ml of tetrahydrofuran, 27 ml of methylene chloride and 0.99 ml of N-methyl-morpholine cooled to −20° C. and after standing at −20° C. for 3 minutes, the mixture was cooled to −35° C. and a solution of 2.45 g of 7-aminocephalosporanic acid in 45 ml of methylene chloride and 252 ml of triethylamine were added thereto. The mixture stood for 2½ hours with spontaneous heating and was then evaporated to dryness. The residue was taken up in a mixture of methylene chloride, water and N hydrochloric acid with a pH of 1-2 and the mixture was extracted with methylene chloride. The organic extracts were washed with water, dried and vacuum filtered. The filtrate was evaporated to dryness and the residue was taken up in ethyl acetate. The solution was diluted with isopropyl ether and was stirred and vacuum filtered The recovered product was rinsed with isopropyl ether and dri to obtain 4.87 g of the anti isomer of 3-acetoxymethyl-7-[2-(2-tritylamino-4-thiazolyl)-2-ethoxyiminoacetamido]-ceph-3-em-4-carboxylic acid. The said product was dissolved in 10 ml of hot ethyl acetate and the solution was slowly diluted with isopropyl ether. The mixture was stirred and was vacuum filtered and the recevered product was rinsed with isopropyl ether and dried to obtain 4.53 g of purified product.

EXAMPLE 15

Anti isomer of 3-acetoxymethyl-7-[2-(2-amino-4-thiazolyl)-2-ethoxyiminoacetamido]-ceph-3-eme-4-carboxylic acid A mixture of 4.27 g of the purified product of Example 14 in 20 ml of 50% aqueous formic acid was stirred on a water bath heated at 60° C. for 20 minutes and was then cooled and diluted with water. The mixture was stirred for 10 minutes and was vacuum filtered to remove triphenylcarbinol which was rinsed with water to obtain a final weight of 1.44 g. The filtrate was added to ethanol and was evaporated to dryness. The residue was dissolved in ethanol and the solution was again evaporated to dryness under reduced pressure. The residue was added to 30 ml of water and the mixture was stirred for an hour in an ice bath and was then vacuum filtered. The recovered product was rinsed and dried to obtain 2.06 g of 3-acetoxymethyl-7-[2-(2-amino-4-thiazol -2-ethoxyiminoacetamido]-ceph-3-eme-4-carboxylic acid.

The product was purified by dissolving it in 5 ml of water and 5 ml of 10% aqueous sodium bicarbonate solution and the mixture was vacuum filtered. The filter was rinsed with water and the filtrate was adjusted to a pH of 3–4 by dropwise addition of formic acid. After standing at room temperature for 12 hours, the mixture was vacuum filtered and the recovered crystals were rinsed with water and dried to obtain 1.73 g of pure product melting at about 200° C. with decomposition.

RMN Spectrum (60 MHZ DMSO) ppm: 2.04 ($CH_3CO$—) and 7.5 (proton of thiazole ring).

EXAMPLE 16

Anti isomer of 3-acetoxymethyl-7-[2-(2-tritylamino-4-thiazolyl]-2-(1-methylethoxyimino)-acetamido]-ceph-3-eme-4-carboxylic acid

STEP A: Anti isomer of ethyl 2-(2-tritylamino-4-thiazolyl)-2-(1-methylethoxyimino)-acetate.

A mixture of 6.86 g of the anti isomer of ethyl-2-(2-tritylamino-4-thiazolyl)-2hydroxyiminoacetate of Example 14, 3.51 g of potassium carbonate in 15 ml of dimethylformamide and 7.7 ml of isopropyl iodide was held under an argon atmosphere and stirring for 4½ hours and then 250 ml of distilled water and 150 ml of ethyl acetate were added there with stirring. The mixture was decanted and the aqueous phase was washed with water and was extracted with ethyl acetate. The organic phase was dried, vacuum filtered and evaporated to dryness. The residue was taken up in ethanol and crystallization started after seeding. The mixture was vacuum filtered and the precipitate was rinsed with ethanol and empasted with petroleum ether to obtain 3.26 g of the anti isomer of ethyl 2-(2-tritylamino-4-thiazolyl)-2-(1-methylethoxyimino)-acetate melting at 182° C.

STEP B: Anti isomer of 2-(2-tritylamino-4-thiazolyl-2-(1-methylethoxyimino)-acetic acid A mixture of 6.8 g of the product of Step A, 41 ml of dioxane and 8.15 ml of 2N sodium hydroxide was heated on a water bath at 55° C. for 2 hours and was then cooled. 9.5 ml of 2N hydrochloric acid were added to obtain a pH of 2–3 and the dioxane was distilled. Crystallization was effected and water diluted the mixture under stirring. The recovered precipitate was vacuum filtered, rinsed with water, empasted with ether and dried to obtain 5.87 g of the anti isomer of 2-(2-tritylamino-4-thiazolyl)-2-(1-methylethoxyimino)-acetic acid melting at 240° C. (decomp.).

RMN ($CDCl_3$, 60 MHZ) ppm: =7.66 (proton of thiazolic ring) and 7.31 (trityl group).

STEP C: Anti isomer of 3-acetoxymethyl-7-[2-(2-tritylamino-4-thiazolyl)-2-(1-methylethoxyimino)-acetamido]-ceph-3-eme-4-carboxylic acid A mixture of 5.66 g of the product of Step B, 48 ml of tetrahydrofuran, 48 ml of methylene chloride and 1.32 ml of N-methyl-morpholine was heated until dissolution and was then cooled to −20° C. 1.56 ml of isobutyl chloroformate were added and the mixture stood at −10° to −20° C. for 10 minutes and was then cooled to −35° C. A mixture of 3.26 g of 7-amino-cepholsporanic acid, 60 ml of methylene chloride and 3.36 ml of dry triethylamine were added all at once and the mixture was heated with stirring for 3½ hours. The solvents were distilled and the residue was totally dissolved in the ethyl acetate and the solution was diluted with isopropyl ether and was stirred and vacuum filtered. The recovered precipitate was rinsed with isopropyl ether and dried to obtain 5.42 g of product. 5.82 g of the latter was dissolved in 20 ml of hot ethyl acetate and the solution was diluted with 200 ml of isopropyl ether, then vacuum filtered. The precipitate was dried to obtain 4.82 g of the anti isomer of 3-acetoxymethyl-7-[2-(2-tritylamino-4-thiazolyl)-2-(1-methylethoxyimino)acetamido]-ceph-3-eme-4-carboxylic acid.

EXAMPLE 17

Anti isomer of 3-acetoxymethyl-7-[2-(2-amino-4-thiazolyl)-2-(1-methylethoxyimino)-acetamido]-ceph-3-eme-4-carboxylic acid A mixture of 3.62 g of the product of Example 16 and 16 ml of 50% aqueous formic acid was held at 60° C. for 20 minutes was then cooled at 20° C. 16 ml of water were added and the mixture was stirred and vacuum filtered. The precipitate was rinsed and dried to obtain 1.23 g of triphenylcarbinol. The filtrate was evaporated to dryness under reduced pressure and the residue was taken up in ethanol which solution was evaporated to dryness under reduced pressure. The residue was taken up in water and the mixture was stirred and then cooled to induce crystallization. The mixture was vacuum filtered and the gummy crystals were rinsed with water and dried to obtain 1.68 g of raw product.

A solution of 2 g of the latter product in 5 ml of water an 5 ml of 5% aqueous sodium bicarbonate solution was stirred for 10 minutes and the mixture was vacuum filtered. The precipitate was rinsed with water and the pH of the filtrate was adjusted to 3 with formic acid. The mixture was stirred for an hour in an ice bath and the mixture was vacuum filtered. The recovered gum was rinsed with water and was dissolved in 10 ml of hot ethanol. The solution was cooled with ice water and was vacuum filtered. The precipitate was rinsed with ethanol and then with ether to obtain 748 of the anti isomer of 3-acetoxymethyl-7-[2-(2-amino-4-thiazolyl)-2-(1-methylethoxyimino)-acetamido]-ceph-3-eme-4-carboxylic acid. A formation of a crystalline deposit formed in the filtrate which was diluted with ether without precipitation. The mixture was vacuum filtered and the recovered crystals were rinsed with a mixture of ether and ethanol and then with ether to obtain another 177 mg of pure product which melted at about 200° C. with decomposition.

RMN (DMSO 60 HMZ) ppm: =7.46 (proton of thiazole ring) and 4.43 (tertiary proton of isopropyl).

EXAMPLE 18

Anti isomer of 3-acetoxymethyl-7-[2-(2-tritylamino-4-thiazolyl)-2-(2-propenyloxyimino)-acetamido]-ceph-3-eme-4-carboxylic acid

STEP A: Anti isomer of ethyl 2-(2-tritylamino-4-thiazolyl)-2-(2-propenyloxyimino)-acetate A mixture of 6.86 g of the anti isomer of ethyl 2-(2-tritylamino-4-thiazolyl)-2-hydroxyiminoacetate [Step A of Example 14], 3.51 g of potassium carbonate, 15 ml of dimethylformamide and 7 ml of allyl iodide was stirred under an inert atmosphere at room temperature for 5 hours and then 250 ml of water and 150 ml of ethyl acetate were added thereto with stirring. The mixture was decanted and the aqueous phase was washed and reextracted with ethyl acetate. The extracts were dried, vacuum filtered and evaporated to dryness. The residue was taken up in ethanol and crystallization was started. The mixture was cooled in an ice bath with stirring for half an hour and was then vacuum filtered. The crystals were rinsed with ethanol to obtain 4.72 g of the anti isomer of ethyl 2-(2-tritylamino-4-thiazolyl)-2-(2-propenyloxyimino)-acetate. 215 mg of the product were dissolved in 2 ml of ethanol and 2 ml of methylene chloride and the mixture was filtered. The filtrate was concentrated and diluted with ethanol. Crystallization was effected in an ice bath and the mixture was vacuum filtered. The crystals were rinsed with ethanol and dried to obtain 70 mg of the pure product which melted at 90° C. (pasty) and 160° C. (pure).

STEP B: Anti isomer of 2-(2-tritylamino-4-thiazolyl)-2-(2-propenyloxyimino)-acetic acid A mixture of 3.71 g of the product of Step A, 22 ml of dioxane and 4.5 ml of 2N sodium hydroxide was heated in a water bath at 55° C. for 110 minutes and was then cooled. 5.25 ml of 2N hydrochloric acid were added thereto to adjust the pH to 2 and the dioxane was evaporated. The gummy residue was diluted with water and the mixture was cooled in an ice bath and was vacuum filtered. The recovered precipitate was rinsed with water and empasted 3 times with ether to obtain 2.85 g of the anti isomer of 2-(2-tritylamino-4-thiazolyl)-2-(2-propenyloxyimino)-acetic acid melting at 198° C. (decomp.)

RMN (CDCl$_3$ 90 MHZ) ppm:=7.64 (proton of thiazole ring) and 7.27 (trityl proton).

STEP C: Anti isomer of 3-acetoxymethyl-7-[2-(2-tritylamino-4-thiazolyl)-2-(2-propenyloxyimino)-acetamido]-ceph-3-eme-4-carboxylic acid 0.78 ml of isobutyl chloroformate were added at −20° C. to a mixture of 2.82 g of the product of Step B, 24 ml of dry tetrahydrofuran and 24 ml of methylene chloride to which 0.66 ml of N-methyl-morpholine had been added and the mixture was stirred at −20° C. for 3 minutes. The mixture was then cooled to −35° C. and a solution of 1.63 g of 7-amino-cephalosporanic acid 30 ml of methylene chloride and 1.68 ml of triethylamine was added thereto. The mixture was returned to room temperature during 3 hours and was evaporated to dryness. The residue was taken up in methylene chloride, and 50 ml of water and 15 ml of N hydrochloric acid were added. The mixture was stirred, decanted, and washed with water. The mixture was extracted with methylene chloride and the extracts were dried and vacuum filtered. The filter was rinsed with methylene chloride and the filtrate was evaporated to dryness. The residue was taken up in ethyl acetate and the solution was diluted with isopropyl ether, was stirred and was vacuum filtered. The recovered precipitate was rinsed with isopropyl ether to obtain 3.08 g of the anti isomer of 3-acetoxymethyl-7-[2-(2-tritylamino-4-thiazolyl)-2-(2-propenyloxyimino)-acetamido]-ceph-3-eme-4-carboxylic acid. 3.59 g of the said product were dissolved in 15 ml of ethyl acetate and the solution was diluted with isopropyl ether, was stirred and was vacuum filtered to obtain 3.33 g of the said purified product.

EXAMPLE 19

Anti isomer of 3-acetoxymethyl-7-[2-(2-amino-4-thiazolyl)-2-(2-propenyloxyimino)-acetamido]-ceph-3-eme-4-carboxylic acid A mixture of 2.53 g of the product of Example 18 in 11.5 ml of a 50% aqueous formic acid solution was heated at 60° C. for 20 minutes and was then diluted with water and cooled to room temperature. The mixture was vacuum filtered and the solids were rinsed with water and dried to obtain 963 mg of triphenylcarbinol. The filtrate and wash waters were evaporated to dryness under reduced pressure and the residue was taken up in ethanol. The solution was evaporated to dryness and the gum residue was taken up in 15 ml of water. The mixture effloresced and was vacuum filtered. The solid was rinsed with water and dried to obtain 1.275 g of product. A suspension of 1.63 g of the said raw product in 15 ml of ethanol was refluxed and was then vacuum filtered. The precipitate was rinsed with ethanol to obtain 877 mg of insoluble product. 20 ml of ether were added to the filtrate and the mixture was vacuum filtered. The solids were rinsed with a 1-1 ethanol-ether mixture and were dried to obtain a second crop of 97 mg. The filtrate was concentrated at which time crystallization occured. The product was recovered by vacuum filtration, was rinsed with ethanol then with ether and dried to obtain 162 mg of pure anti isomer of 3-acetoxymethyl-7-[2-(2-amino-4-thiazolyl)-2-(2-propenyloxyimino)-acetamido]-ceph-3-eme-4-carboxylic acid with a melting point of 180° C. (pasty).

RMN (DMSO 60 MHZ) p.p.m.=7.48 (thiazole ring proton) and 2.04 (proton of acetyl).

EXAMPLE 20

Syn isomer of 3-acetoxymethyl-7-[2-(2-amino-4-thiazolyl)-2-methoxyiminoacetamido]-ceph-3-eme-4-carboxylic acid STEP A: Syn isomer of ethyl 2-(2-chloroacetamido-4-thiazolyl)-2-methoxyiminoacetate A mixture of 45.8 g of the syn isomer of ethyl 2-(2-amino-4-thiazolyl)-2-methoxyiminoacetate (Step A of Example 3) in 200 ml of methylene chloride was heated to distill 20 ml and was then cooled to 10° C. 50 ml of pyridine were added to the mixture followed by the addition of 41 g of monochloroacetic acid anhydride and the mixture was heated until dissolution occured. The mixture stood at 20° C. under nitrogen for 6 hours and 5 ml of water were added with stirring. The mixture was poured into 300 ml of iced 2N hydrochloric acid and was then decanted. The aqueous phase was extracted with methylene chloride and the organic extracts were washed with water, with sodium bicarbonate solution and then with water, was dried, treated with carbon black and was concentrated. 300 ml of isopropyl ether were added thereto and the product crystallized. The mixture was concentrated to obtain a thick paste which was iced and vacuum filtered. The solid was washed with isopropyl ether and dried to obtain 45.4 g of the syn isomer of ethyl 2-(2-chloroacetamido-4-thiazolyl)-2-methoxyiminoacetate melting at 113° C. A sample was crystallized from an isopropyl ether-methylene chloride mixture to obtain a product melting at 118° C.

RMN (CDCl₃ 60 MHz) (a) triplet center about 1.38 ppm J=7 Hz; (b) singulet 4.05 ppm; (c) quadruplet center about 4.44 ppm J=7 Hz; (d) singulet 4.33 ppm; (e) singulet 7.27 ppm; and (f) singulet 9.95 ppm.

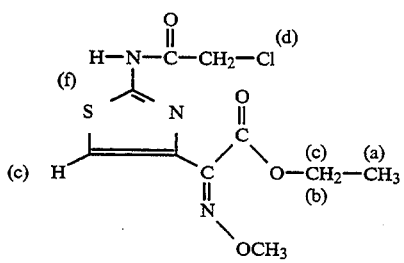

STEP B: Syn isomer of 2-(2-chloroacetamido-4-thiazolyl)-2-methoxyimino-acetic acid 30 ml of pure sodium carbonate solution were added at 20° C. under a nitrogen atmosphere to a mixture of 46 g of the product of Step A in 230 ml of absolute ethanol and the product dissolved. Crystallization of a sodium salt commenced and then the medium became a mass. After 16 hours, the mixture was vacuum filtered and the solid was washed with ethanol. The solid was dissolved in water and after icing, 100 ml of 2N hydrochloric acid were added thereto. The mixture was saturated with sodium chloride and was then extracted with ethyl acetate containing 10% ethanol. The extracts were dried, treated with carbon black and distilled to dryness under reduced pressure. The water was extrained with benzene. The residue was taken up in methylene chloride and the solution was evaporated to dryness. Again, the residue was taken up in methylene chloride and the solution was iced and vacuum filtered. The solid was washed with methylene chloride and dried to obtain 34.5 g of the syn isomer of 2-(2-chloroacetamido-4-thiazolyl)-2-methoxyimino-acetic acid melting at about 200° C. The product was purified by crystallization from an acetone-isopropyl ether mixture.

Analysis: C₈H₈O₄N₃ClS; molecular weight = 277.68

| | | | | | |
|---|---|---|---|---|---|
| Cal-<br>culated: | % 34.60<br>C | % 2.90<br>H | % 15.13<br>N | % 12.77<br>Cl | % 11.55<br>S |
| Found: | 34.8 | 2.8 | 14.8 | 12.6 | 11.5 |

RMN (DMSO 60 MHz): (a) singulet 3.92 ppm; (b) singulet 4.38 ppm; (c) singulet about 5 ppm; (d) singulet 7.58 ppm; and (e) singulet 12.6 ppm.

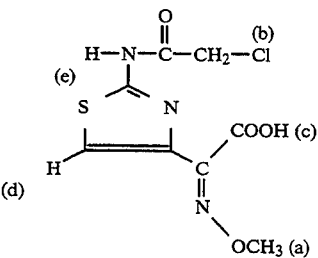

STEP C: Syn isomer of 3-acetoxymethyl-7-[2-(2-chloroacetamido-4-thiazolyl)-2-methoxyimino)-acetamido]-ceph-3-eme-4-carboxylic acid 8 ml of triethylamine were added at 5° C. to a mixture of 15.3 g of the product of Step B in 80 ml of methylene chloride and then 3.8 ml of thionyl chloride and 26 ml of methylene chloride were added thereto at 0° C. The mixture stood for 15 minutes at 0° C. and then 7 ml of triethylamine were added. A mixture of 13.6 g of 7-amino-cephalosporanic acid in 100 ml of methylene chloride and 14 ml of triethylamine were added thereto at 0° C. under nitrogen and after returning the temperature to 20° C., the mixture was stirred for an hour. The mixture was evaporated to dryness under reduced pressure at 30°–35° C. and the residue was dissolved in 250 ml of water. The solution was treated with carbon black and 50 ml of 2N hydrochloric acid were added. The precipitate was recovered by vacuum filtration and was washed with water and was then suspended in 80 ml of ethanol. 7 ml of triethyl amine were added at 5° C. and then 15 ml of 4N sulfuric acid were added all at once with stirring at 5° C. Crystallization was effected for 15 minutes and the mixture was vacuum filtered. The product was washed with ethanol by empasting and then with ether and dried under reduced pressure to obtain 18.6 g of the syn isomer of 3-acetoxymethyl-7-[2-(2-chloroacetamido-4-thiazolyl)-2-methoxyiminoacetamido]-ceph-3-eme-4-carboxylic acid with a specific rotation of $[\alpha]_D^{20} = +26° \pm 1°$ (C=1% in dimethylformamide).

RMN (DMSO 60 MHz): (a) singulet 2.03 ppm; (b) singulet 3.90 ppm; (c) singulet 4.38 ppm; and (d) singulet 7.45 ppm.

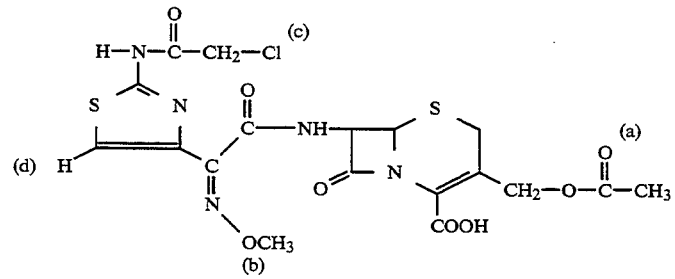

STEP D: Syn isomer of 3-acetoxymethyl-7-[2-(2-amino-4-thiazolyl)-2-methoxyiminoacetamido]-ceph-3-eme-4-carboxylic acid 1 g of potassium bicarbonate was added at 20° C. to a suspension of 5.32 g of the product of Step C in 10.6 ml of water and 912 mg of thiourea and after dissolution, the mixture was stirred at 20° C. under nitrogen for 6 hours. The gummy precipitation started after about 90 minutes and then 30 ml of water and 3 ml of formic acid were added thereto. The mixture was cooled to 5° C. and was vacuum filtered. The product was washed with water containing 10% formic acid and was dissolved at 5° C. in 30 ml of water containing triethylamine. 3 ml of formic acid were added at 5° C. and the mixture was vacuum filtered. The precipitate was empasted with water containing formic acid and the dark brown gum was eliminated. The combined aqueous phases were treated with carbon black to obtain a clear yellow solution whch was saturated with ammonium sulfate and then vacuum filtered. The precipitate was empasted with water, was vacuum filtered and washed with water to obtain a first crop. The mother liquors were saturated with ammonium sulfate to effect precipitation and were vacuum filtered then washed with water to obtain a second crop. The two crops were combined and were taken up in ethanol. The mixture was stirred at 20° C. for an hour and stood for 16 hours at 0° C. The mixture was vacuum filtered and the product was washed with ethanol and then with ether and was dried under reduced pressure to obtain 3.47 g of the syn isomer of 3-acetoxymethyl-7-[2-(2-amino-4-thiazolyl)-2-methoxyiminoacetamido]-ceph-3-eme-4-carboxylic acid identical to that of Examples 4 and 6.

RMN (DMSO 60 MHz): (a) singulet 2.03 ppm; (b) singulet 3.55 ppm; (c) doublet 5.19 ppm J=5 Hz; and (d) singulet 6.8 ppm.

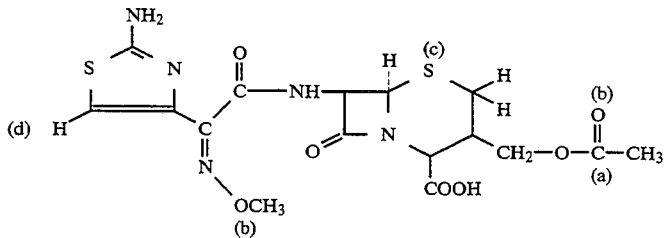

EXAMPLE 21

Diethylamine salt of syn isomer of 3-acetoxymethyl-7-[2-(2-tritylamino-4-thiazolyl)-2-methoxyiminoacetamido]-ceph-3-eme-4-carboxylic acid STEP A: Ethyl 2-acetyl-2-methoxyiminoacetate 6.1 kg of potassium carbonate were added at 20°-25° C. to a mixture of 4.69 kg of ethyl 2-acetyl-2-hydroxyiminoacetate (equal to 4.21 kg of pure product) in 21 liters of anhydrous pure acetone and after stirring the suspension for 10 minutes, 3.72 kg of dimethyl sulfate were added at 20°-25° C. The mixture was poured into 126 liters of demineralized water and was extracted 4 times with 5 liters and then with 2 liters of methylene chloride. The combined extracts were washed with 10 liters of demineralized water, were dried and vacuum filtered. The filter was rinsed with 2 liters of methylene chloride and the filtrate was evaporated to dryness under reduced pressure to obtain 4.88 kg of ethyl 2-acetyl-2-methoxyiminoacetate with an Rf=0.7 (thin layer chromatography-9-methylene chloride-ethyl acetate eluent). The product was identical to that product in Step A of Example 3.

STEP B: Ethyl 4-bromo-2-methoxyimino-acetylacetate

A solution of 2.96 kg of bromine in 3.5 liters of methylene chloride was added over 30 minutes at 22° C. ±1° to a solution of 3.53 kg of the product of Step A in 18.6 liters of methylene chloride and 3.5 g of p-toluene sulfonic acid an hydrobromic acid was released for 15 minutes. The mixture was stirred for 45 minutes at 22° C. The organic phase was washed twice with 14 liters of demineralized water and the wash water was extracted twice with 3.5 liters of methylene chloride. The combined organic phase was dried, filtered, rinsed with methylene chloride and evaporated to dryness under reduced pressure to obtain 4.73 kg of ethyl 4-bromo-2-methoxyimino-acetylacetate.

STEP C: Syn isomer of ethyl 2-(2-amino-4-thiazolyl)-2-methoxyiminoacetate

A mixture of 1.43 kg of thiourea, 3.55 liters of ethanol and 7.1 liters of demineralized water was stirred for 10 minutes at 20° C. and then a mixture of 4.730 kg of the product in Step B in 3.55 liters of ethanol was added thereto at 20°-25° C. The mixture was stirred for 3 hours at 20°-25° C. and was then cooled to 15°-20° C. The mixture was neutralized to a pH of 7 with about 1.6 liters of 22° Bé ammonium hydroxide solution and the mixture was stirred for 15 minutes at 20°-25° C. and was vacuum filtered. The recovered precipitate was washed 5 times with 1.8 liters of demineralized water, and dried to obtain 2.947 kg of the syn isomer of ethyl 2-(2-amino-4-thiazolyl)-2-methoxyiminoacetate melting at 162° C. The melting at 162° C. The product was identical to that of Step A of Example 3.

STEP D: Syn isomer of ethyl 2-(2-tritylamino-4-thiazolyl)-2-methoxyiminoacetate

A mixture of 3.41 kg of the product of Step C, 17 liters of methylene chloride and 2.275 liters of triethylamine was stirred for 15 minutes and then 4.55 kg of trityl chloride were added at 20°-25° C. over one hour with stirring under nitrogen. The mixture was stirred for 20 hours at 20°-25° C. under nitrogen during which triethylamine hydrochloride crystallized and the mixture was washed with 10.2 liters of iced 0.5N hydrochloric acid and twice with 10.2 liters of iced demineralized water and the wash waters were extracted with 1.7 liters of methylene chloride. The combined organic extracts were dried and filtered and the filter was washed with 1.7 liters of methylene chloride. The filtrates were evaporated to dryness under reduced pressure below 50° C. to obtain 8.425 kg of raw product. The latter was dissolved at 20°-25° C. in 8.4 liters of methanol and the solution was stirred for an hour at 20°-25° C. after the addition of 2.8 liters of demineralized water to induce crystallization. The mixture was stirred for another hour and was vacuum filtered. The product was empasted twice with 1.7 liters of methanol containing 25% water and was dried at 40° C. to obtain 7.165 kg of the syn isomer of ethyl 2-(2-tritylamino-4- thiazolyl)-2-methoxyiminoacetate which was identical to the product of Example 3, Step B.

STEP E: Syn isomer of sodium salt of 2-(2-tritylamino-4-thiazolyl)-2-methoxyiminoacetamido A mixture of 4.175 kg of the product of Step D in 20.9 liters of ethanol was refluxed under nitrogen with stirring to obtain total dissolution at 55° C. and then 5.235 liters of about 2N sodium hydroxide were added thereto at reflux under nitrogen. Crystallization was rapid and the mixture was stirred for one hour at reflux under nitrogen and was cooled to 20°–25° C. and held there for 2 hours. The mixture was vacuum filtered and the solid product was washed 4 times with 2.1 liters of ethanol and was dried to obtain 4.02 kg of the syn isomer of sodium salt of 2-(2-tritylamino-4-thiazolyl)-2-methoxyiminoacetamido.

STEP F: Syn isomer of 2-(2-tritylamino-4-thiazolyl)-2-methoxyimino-acetic acid 2 liters of about 1N hydrochloric acid were added in 2 minutes at 20°–25° C. under nitrogen to a mixture of 500 g of the product of Step E (440 g of dry product) in 2.5 liters of methylene chloride and the mixture was stirred under a nitrogen atmosphere for 2 hours. The mixture was decanted and the organic phase was washed 3 times with 2 liters of demineralized water and the wash waters were extracted with 1 liter of methylene chloride. The combined organic phases were dried, treated with 0.25 g of carbon black, vacuum filtered, rinsed with methylene chloride, and evaporated to dryness to obtain 481 g of raw product. The latter was taken up in 2.1 liters of isopropyl ether and the solution was vacuum filtered. The solid product was washed twice with 420 ml of isopropyl ether and was dried under reduced pressure to obtain 424.6 g of the syn isomer of 2-(2-tritylamino-4-thiazolyl)-2-methoxyiminoacetic acid identical to the product of Step C of Example 3.

STEP G: Syn isomer of diethylamine 3-acetoxymethyl-7-[2-(2-tritylamino-4-thiazolyl)-2-methoxyiminoacetamido]-ceph-3-eme-4-carboxylate 1200 ml of methylene chloride were added to 200 g of the product of Step F and the mixture was refluxed with stirring under an inert atmosphere. Then, 600 ml of methylene chloride were distilled at normal pressure and after cooling to 18°–20° C., a solution of 54 g of dicyclohexylcarbodiimide in 54 ml of methylene chloride were added at 18°–20° C. The mixture was stirred under an inert atmosphere for an hour at 18°–20° C. and then an extemporaneously prepared solution of 61.4 g of 7-amino-cephalosporanic acid in 900 ml of methylene chloride and 63 ml of triethylamine were added at that temperature over 15 minutes. The mixture with a pH of 6.5 to 7 was stirred at 20° C. for 90 minutes and 50 ml of acetic acid were added. The mixture was stirred another 15 minutes at 20° C. and was then vacuum filtered. The filter was rinsed 4 times with 200 ml of methylene chloride and the filtrate was washed 3 times with 400 ml of demineralized water and was then dried over magnesium sulfate and was vacuum filtered. The filter was washed twice with 200 ml of methylene chloride and the filtrate was evaporated to dryness under an inert atmosphere with reduced pressure. The dry oily residue was dissolved in 700 ml of dioxane with stirring under an inert atmosphere at 20°–25° C. and the solution was evaporated to dryness under an inert atmosphere with reduced pressure at a temperature below 30° C. The residue was taken up in 300 ml of a dioxane-methylene chloride mixture and then 500 ml of ether were added at 20°±2° C. followed by the addition of 52 ml of diethylamine. After about 10 minutes, crystallization occured and the mixture stood at 20° C. under an inert atmosphere for an hour. The mixture was vacuum filtered and the solid product was rinsed 3 times with 100 ml of a dioxane-ether solution and was dried to obtain 113.6 g of the syn isomer of diethylamine 3-acetoxymethyl-7-[2-(2-tritylamino-4-thiazolyl)-2-methoxyimonoacetamido]-ceph-3-eme-4-carboxylate. 3.25 liters of isopropyl ether were added over 30 minutes to the filtrate and the mixture was stirred for 15 minutes and was then vacuum filtered. The solid product was rinsed twice with 400 ml of isopropyl ether and was dried under reduced pressure to obtain 182 g of product identical to that of Example 5.

EXAMPLE 22

Syn isomer of 3-acetoxymethyl-7-[2-(2-amino-4-thiazolyl)-2-methoxyiminoacetamido]-ceph-3-eme-4-carboxylic acid A mixture of 182 g of the product of Example 21 in 347 ml of formic acid and 87 ml of demineralized water was stirred under an inert atmosphere at 28°–30° C. until there was total dissolution followed by crystallization of triphenyl carbinol and the mixture was stirred for another 2½ hours at 28°–30° C. under argon. Precipitation was effected with 1740 ml of demineralized water and 847 g of ammonium sulfate for 15 minutes with stirring and then the mixture was stirred for 30 minutes and was then vacuum filtered. The solid product was rinsed twice with 174 ml of demineralized and was dried under reduced pressure at 25°–30° C. to obtain 147 g of a mixture of product and triphenyl carbinol. The raw product was empasted with ether for an hour at 18°–20° C. and was then vacuum filtered. The product was rinsed twice with 147 ml of ether and then dried at 25°–30° C. to obtain 89 g of product which was empasted with stirring under nitrogen with 445 ml of ethanol. The suspension was stirred for an hour at 45°–50° C. and one hour at 18°–20° C. and was then vacuum filtered. The product was rinsed twice with 45 ml of ethanol and was dried under reduced pressure at 20° C. to obtain 76.85 g of the syn isomer of 3-acetoxymethyl-7-[2-(2-amino-4-thiazolyl)-2-methoxyiminoacetamido]-ceph-3-eme-4-carboxylic acid.

The latter product in 230 ml of acetic acid was stirred for 15 minutes under nitrogen and then 77 ml of demineralized water were added thereto followed by the addition of about 700 ml of water. The mixture was stirred for an hour at 18°–20° C. and 269 g of ammonium sulfate were added over 10 minutes. The mixture stood for 15 minutes and 3.85 g of carbon black were added. The mixture was stirred for 15 minutes and was then vacuum filtered. The product was rinsed with 77 ml of demineralized water containing 25% of acetic acid and 154 ml of formic acid were added with stirring at 18°–20° C. to the filtrate. A seed of the final product was added to induce crystallization by scratching and the mixture was stirred for 2 hours at 18°–20° C. and then 2 hours at 0° to 5° C. The mixture was vacuum filtered and the product was washed 4 times with 77 ml of demineralized water containing 5% formic acid and was dried under reduced pressure at 20°–25° C. to obtain 49.45 g of the said product in the form of its formate. The latter was empasted with 250 ml of ethanol with stirring for an hour at 45°–50° C. and then 1 hour at 18°–20° C. The mixture was vacuum filtered and the product was rinsed twice with 50 ml of ethanol and dried at 20° C. under reduced pressure and then at 35°–40° C. for 10 to 15 hours to obtain 45.45 g of the said product with a specific rotation $[\alpha]_D^{20} = +64.5°$ (C=0.5% in water with 0.5% NaHCO₃). The product was identical to that of Examples 4, 6 and 20.

EXAMPLE 23

Cristallize syn isomer of sodium 3-acetoxymethyl-7-[2-(2-amino-4-thiazolyl)-2-methoxyiminoacetamido]-ceph-3-eme-4-carboxylate A solution of 19.8 g of the product of Example 22 in 65 ml of a molar solution of sodium acetate in methanol stood at room temperature for 35 minutes for crystallization and then 40 ml of ethanol were added thereto over an hour. The mixture was stirred in an ice bath for 2½ hours and was then vacuum filtered. The product was washed twice with 10 ml of a 1-1 methanol-ethanol mixture and twice with 10 ml of ethanol and finally twice with 20 ml of ether. The product was dried for 2 hours under reduced pressure at 45° C. and 48 hours under reduced pressure in the presence of sulfuric acid to obtain 16.191 g of crystals of the syn isomer of sodium 3-acetoxymethyl-7-[2-(2-amino-4-thiazolyl)-2-methoxyiminoacetamido]-ceph-3-eme-4-carboxylate.

By operating while avoiding contact with atmospheric humidity, the physical properties of the product were: 0.2% of water (Karl Fischer); ≦0.1% methanol and; 0.45% ethanol with the latter two values being determined by vapor phase chromatography.

Analysis: $C_{16}H_{16}O_7N_5S_2Na$; molecular weight = 477.5

| | % C | % H | % N | % S | % Na |
|---|---|---|---|---|---|
| Calculated: | 40.24 | 3.38 | 14:67 | 13.43 | 4.81 |
| Found: | 39.9 | 3.5 | 14.5 | 13.1 | 4.8 |

The product rehydrated when standing in air. The x-ray spectrum (Debye Scherrer) confirmed the crystalline nature of the product. Isopropanol in place of ethanol was equally useful for the crystallization.

EXAMPLE 24

Cristallize syn isomer of sodium 3-acetoxymethyl-7-[2-(2-amino-4-thiazolyl)-2-methoxyiminoacetamido]-ceph-3-eme-4-carboxylate STEP A: Solvate of formic acid and syn isomer of 3-acetoxymethyl-7-[2-(2-amino-4-thiazolyl)-2-methoxyiminoacetamido]-ceph-3-eme-4-carboxylate 87.2 g of the diethylamine salt of 3-acetoxymethyl-7-[2-(2-tritylamino-4-thiazolyl)-2-methoxyiminoacetamido]-ceph-3-eme-4-carboxylic acid of Example 5 was added in small amounts with stirring to a mixture of 220 ml of formic acid and 220 ml water and the mixture was stirred at 50° C. for 30 minutes and was then cooled. The mixture was filtered to remove 30.1 g of triphenyl carbinol and the filtrate was poured into 450 ml of water. The mixture was treated with carbon and filtered and the filter was evaporated at 40° C. under reduced pressure until a precipitate formed. 200 ml of anhydrous ethanol were added and the mixture was cooled with ice and was filtered. The precipitate was washed with ethanol and with ether and was dried under redued pressure to obtain 31.1 g of a solvate of formic acid and the syn isomer of 3-acetoxymethyl-7-[2-(2-amino-4-thiazolyl)-2-methoxyiminoacetamido]-ceph-3-eme-4-carboxylic acid.

Analysis: $C_{16}H_{17}N_5O_7S_2 \cdot HCOOH \cdot H_2O$; molecular weight = 541.5

| | % C | % H | % N | % S | % H₂O |
|---|---|---|---|---|---|
| Calculated: | 39.3 | 4.08 | 13.48 | 12.34 | 3.46 |
| Found: | 39.2 | 4.1 | 13.2 | 12.8 | 4.15 |

STEP B: Crystallize sodium salt of the syn isomer of 3-acetoxymethyl-7-[2-(2-amino-4-thiazolyl)-2-methoxyiminoacetamido]-ceph-3-eme-4-carboxylic acid A solution of 15 g of the freshly prepared solvate of Step A in 75 ml of ethanol was treated with 4.5 g of potassium acetate and 3 g of active carbon and was then filtered. 5 ml of isopropanol were added with stirring to the filtrate and after standing at 0° C. for 15 hours, the mixture was filtered. The crystals were washed with ethanol and ether and dried for 2 hours at 50° C. under reduced pressure to obtain 7.95 g of the syn isomer of sodium 3-acetoxymethyl-7-[2-(2-amino-4-thiazolyl)-2-methoxyiminoacetamido]-ceph-3-eme-4-carboxylate. The product stood briefly in free and was then analyzed.

Analysis: $C_{16}H_{16}N_5NaO_7S_2 \cdot H_2O$; molecular weight = 495.5

| | % C | % H | % N | % Na | % S |
|---|---|---|---|---|---|
| Calculated: | 38.78 | 3.66 | 14.14 | 4.64 | 12.94 |
| Found: | 38.6 | 3.7 | 13.8 | 4.6 | 13.2 |

EXAMPLE 25 amorphous syn isomer of sodium 3-acetoxymethyl-7-[2-(2-amino-4-thiazolyl)-2-methoxyiminoacetamido]-ceph-3-eme-4-carboxylate STEP A: Solvate of ethanol and syn isomer of 3-acetoxymethyl-7-[2-(2-amino-4-thiazolyl)-2-methoxyiminoacetamido]-ceph-3-eme-4-carboxylic acid A solution of 52 g of the solvate of formic acid obtained in Step A of Example 24 in 3 liters of 96% ethanol and 350 ml of water was concentrated under reduced pressure to obtain a value of about 300 ml and the solvate began to crystallize during the concentration. The mixture was cooled for an hour in an ice bath and was filtered. The precipitate was washed with a little ethanol and was dried at room temperature under reduced pressure in the presence of concentrated sulfuric acid to obtain 44 g of the solvate of ethanol and the syn isomer of 3-acetoxymethyl-7-[2-(2-amino-4-thiazoly)-2-methoxyiminoacetamido]-ceph-3-eme-4-carboxylic acid.

Analysis: $C_{16}H_{17}N_5O_7S_2 \cdot 0.8\ C_2H_5OH$; molecular weight = 492.3

| | % C | % H | % N | % S |
|---|---|---|---|---|
| Calculated: | 42.94 | 4.46 | 14.23 | 13.02 |
| Found: | 43.0 | 4.4 | 14.1 | 12.9 |

STEP B: Amorphous sodium salt

A mixture of 3 g of the solvate of Step A in 60 ml of water was cooled to 0° C. and a solution of 0.504 g of sodium bicarbonate in 6 ml of water was added thereto. The neutral solution was filtered and lyophilysed immediated. After standing briefly in free air the product was analyzed.

| Analysis: C₁₆H₁₆N₅NaO₇S₂ 1.5 H₂O; molecular weight = 504.47 | | | |
|---|---|---|---|
| Calculated: | % C 38.09 | % H 3.8 | % N 13.85 |
| Found: | 38.2 | 3.9 | 13.6 |

EXAMPLE 26

Cristallize syn isomer of sodium
3-acetoxymethyl-7-[2-(2-amino-4-thiazolyl)-2-methoxyiminoacetamido]-ceph-3-eme-4-carboxylate 0.25 ml of n-butanol were slowly added with stirring to a solution of 0.5 g of the amorphous salt of Example 25 in 2 ml of methanol and the mixture was held at 6° C. for 48 hours. The crystals were washed with a little cold methanol and was dried for 3 hours at 40° C. under reduced pressure in the presence of concentrated sulfuric acid to obtain 0.2 g of the above crystalline sodium salt. The product was analyzed after briefly being exposed to air.

| Analysis: C₁₆H₁₆N₅NaO₇S₂.1.5 H₂O; molecular weight = 504.4 | | | | |
|---|---|---|---|---|
| Calculated: | % C 38.09 | % H 3.8 | % N 13.88 | % O 29.96 |
| Found: | 38.4 | 3.8 | 13.8 | 27.1 |

Under analogous operating conditions, slightly different crystalline forms were obtained containing 0.1 mole of methanol and 0.5 or 1 mole of water. The x-ray spectra (Debye Scherrer of the products confirmed there nature.

EXAMPLE 27

Crystalline syn isomer of sodium
3-acetoxymethyl-7-[2-(2-amino-4-thiazolyl)-2-methoxyiminoacetamido]-ceph-3-eme-4-carboxylate A mixture of 4.95 g of the product of Example 22 in 5 ml of ethanol was stirred on an ice bath and 10 ml of a molar solution of aqueous sodium bicarbonate were added. After dissolution, 15 ml of ethanol were added and the mixture was evaporated to dryness under reduced pressure at 30° C. The residue was taken up in 15 ml of methanol and crystallization was induced. The mixture stood overnight in the refrigerator to obtain 3.407 g of the sodium salt identical to the product of Example 23.

EXAMPLE 28

Syn isomer of
7-[2-(2-amino-4-thiazolyl)-2-hydroxyiminoacetamido]-3-acetoxymethyl-ceph-3-eme-4-carboxylic acid

STEP A: Syn isomer of ethyl 2-(2-amino-4-thiazolyl)-2-hydroxyimino-acetate 2 g of ethyl 4-chloro-2-hydroxyimino-acetyl acetate were added over 5 minutes to a solution of 0.8 g of thiourea in 2.4 ml of ethanol and 4.8 ml of water and the mixture was stirred for one hour at room temperature. The majority of the ethanol was distilled off under a partial pressure and the mixture was adjusted to a pH of 6 by addition of solid sodium bicarbonate. The mixture was iced and vacuum filtered and the recovered product was washed with water and dried under reduced pressure at 40° C. to obtain 1.32 g of ethyl 2-(2-amino-4-thiazolyl)-2-hydroxyimino-acetate melting at 232° C.

| Analysis: C₅H₉O₃N₃S | | | | |
|---|---|---|---|---|
| Calculated: | % C 39.06 | % H 4.21 | % N 19.52 | % S 14.9 |
| Found: | 38.9 | 4.4 | 19.7 | 14.6 |

RMN (DMSO, 60 MHz): (a) triplet centered about 1.25 ppm J=7 Hz; (b) quadruplet centered about 4.27 ppm J=7 Hz; (c) singulet at 6.83 ppm; (d) singulet at 7.11 ppm; (e) singulet at 11.4 ppm.

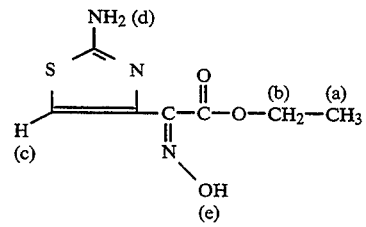

STEP B: Syn isomer of 2-(2-amino-4-thiazolyl)-2-hydroxyimino-acetic acid

A mixture of 21.5 g of the product of Step A, 200 ml of absolute ethanol and 55 ml of 2N sodium hydroxide was stirred for 45 minutes on a water bath at 45° C. and was then placed in an ice water bath. The pH was adjusted to 6 with acetic acid and a precipitation was observed and the mixture was vacuum filtered. The recovered product was rinsed with a 1-1 ethanol-water mixture and then with ether and dried to obtain 16.9 g of the syn isomer of 2-(2-amino-4-thiazolyl)-2-hydroxyimino-acetic acid with an Rf=0.05 (eluant—70-20-10 ethyl acetate-ethanol-water).

STEP C: Sodium salt of syn isomer of 2-(2-tritylamino-4-thiazolyl)-2-tritylhydroxyimino-acetic acid A mixture of 16.9 g of the acid of Step B, 50 ml of dimethylformamide and 42 ml of triethylamine was stirred at room temperature for 15 minutes to effect total dissolution and the mixture was cooled to −20° C. to partially crystallize the triethylamine salt. A mixture of 54 g of trityl chloride in 100 ml of chloroform was added over 15 minutes at −20° C. to the mixture which was then stirred for an hour during which the temperature returned to room temperature. The mixture was poured into 200 ml of water containing 40 ml of 2N hydrochloric acid. The mixture was decanted and the organic phase was washed twice with 200 ml of water, was dried and vacuum filtered. The filtrate was evaporated to dryness under reduced pressure and the residue was taken up in ethyl acetate. 100 ml of a saturated aqueous sodium bicarbonate solution was added thereto and the mixture was stirred and decanted. Crystallization occured while icing for 30 minutes and the mixture was vacuum filtered. The recovered product was rinsed with ethyl acetate to obtain 27 g of sodium 2-(2-tritylamino-4-thiazolyl)-2-tritylhydroxylimino-acetate with a Rf=0.33 (ether).

STEP D: Syn isomer of tert.-butyl 7-[2-(2-tritylamino-4-thiazolyl)-2-tritylhydroxyimino-acetamido]-3-acetoxymethyl-ceph-3-eme-4-carboxylate A mixture of 17.2 g of the sodium salt of Step C, 170 ml of chloroform and 170 ml of N hydrochloric acid was decanted and the organic phase was washed 5 times with water, dried and vacuum filtered. The filtrate was evaporated to dryness and the residue was taken up in 170 ml of methylene chloride. 2.8 g of dicyclohexyl-dicarbodiimide were added thereto and the mixture was stirred for an hour after which it was vacuum filtered to remove 1.9 g of dicyclohexylurea. 3.66 g of tert.-butyl 7-amino-3-acetoxymethyl-ceph-3-eme-4-carboxylate were added to the filtrate and the mixture was stirred for 2 hours at room temperature. The mixture was washed with N hydrochloric acid, with water, with an aqueous 5% sodium bicarbonate solution and finally with water. The organic phase was dried and vacuum filtered and the filtrate was evaporated to dryness. The residue was taken up in methylene chloride and the solution was chromatographed over silica gel. Elution was effected with methylene chloride containing 5% ether and the fractions with an Rf=0.78 in ether were combined and evaporated to dryness under reduced pressure. The residue was taken up in isopropyl ether and effloresced. The mixture was vacuum filtered and the product was rinsed with isopropyl ether to obtain 5.8 g of the syn isomer of tert.-butyl 7-[2-(2-tritylamino-4-thiazolyl)-2-tritylhydroxyimino-acetamido]-3-acetoxymethyl-ceph-3-eme-4-carboxylate.

| Analysis: $C_{57}H_{51}O_7H_5S_2$ | | | | |
|---|---|---|---|---|
| Calculated: | % C 69.7 | % H 5.2 | % N 7.1 | % S 6.5 |
| Found: | 70.4 | 5.6 | 6.5 | 5.9 |

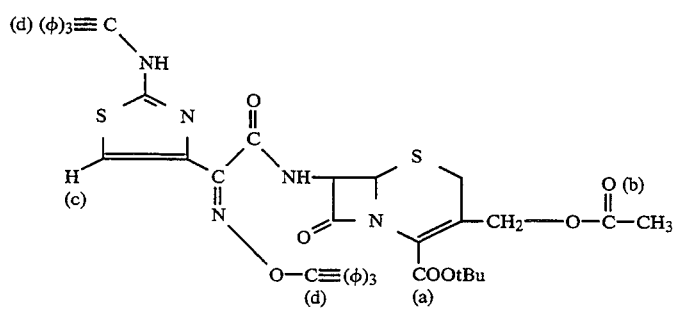

STEP E: Syn isomer of 7-[2-(2-amino-4-thiazolyl)-2-hydroxyimino-acetamido]-3-acetoxymethyl-ceph-3-eme-4-carboxylic acid A mixture of 1 g of the product of Step D in 3 ml of trifluoroacetic acid was stirred at room temperature for 30 minutes and then 30 ml of isopropyl ether were added thereto The mixture was vacuum filtered to recover the precipitated salt which was rinsed with isopropyl ether to obtain 0.652 g of the salt of trifluoroacetic acid and 7-[2-(2-amino-4-thiazolyl)-2-tritylhydroxyimino-acetamido]-3-acetoxymethylceph-3-eme-4-carboxylic acid. The said salt was dissolved in 6 ml of tetrahydrofuran and 3 ml of 50% aqueous formic acid were added thereto. The mixture was stirred at 50° C. for 15 minutes and was evaporated to dryness. The residue was taken up in ether and the mixture was filtered. The product was rinsed with ether to obtain 0.441 g of the formate of the product which was triturated with 2 ml of water containing 3 drops of pyridine (pH≃6). The mixture was vacuum filtered and the product was rinsed with water and dried to obtain 0.136 mg of the syn isomer of 7-[2-(2-amino-4-thiazolyl)-2-hydroxyimino-acetamido]-3-acetoxymethyl-ceph-3-eme-4-carboxylic acid. The filtrate was evaporated to dryness and the residue was taken up in ether. The mixture was vacuum filtered and the product was rinsed with ethanol to obtain another 0.04 g of the said syn isomer.

RMN (DMSO, 60 MHz): a) singulet at 2.01 ppm; b) singulet at 6.67 ppm; c) singulet at 7.08 ppm and d) singulet at 11.3 ppm.

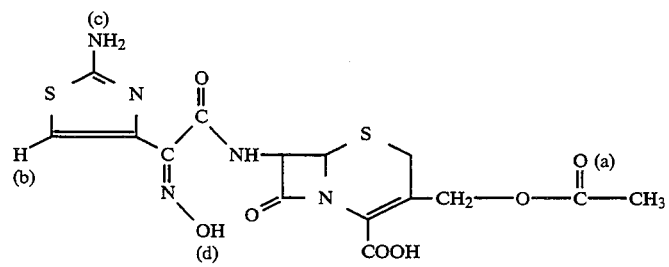

EXAMPLE 29

Syn isomer of 7-[2-(2-amino-4-thiazolyl)-2-hydroxyiminoacetamido]-3-acetoxymethyl-ceph-3-eme-4-carboxylic acid

STEP A: Syn isomer of ethyl 2-(2-tritylamino-4-thiazolyl)-2-hydroxyimino-acetate 32 ml of triethylamine were added to a mixture of 43.2 g of the syn isomer of ethyl 2-(2-amino-4-thiazolyl)-2-hydroxyimino-acetate in 120 ml of dry dimethylformamide cooled to −35° C. and then 60 g of trityl chloride were added thereto in small fractions over 30 minutes. The temperature returned to room temperature during which total dissolution occured and the mixture was heated to 30° C. for an hour. The mixture was poured into 1.2 liters of iced water containing 40 ml of 22° Bé hydrochloric acid and the mixture was stirred on an ice bath and was then vacuum filtered. The precipitate was rinsed with N hydrochloric acid and was empasted with ether to obtain 69.3 g of a hydrochloride salt. The product was dissolved in 5 volumes of methanol to which was added 120% of triethylamine and 5 volumes of water were added to crystalize the syn isomer of ethyl 2-(2-tritylamino-4-thiazolyl)-2-hydroxyimino-acetate.

Analysis: $C_{26}H_{23}O_3N_3S.1/4\ H_2O$

| | %C | %H | %N | %S |
|---|---|---|---|---|
| Calculated: | 67.6 | 5.1 | 9.1 | 6.9 |
| Found: | 67.5 | 5.1 | 8.8 | 6.8 |

RMN (CDCl$_3$, 60 MHz): a) triplet centered about 1.31 ppm, J=7 Hz; b) quadruplet centered about 4.37 ppm, J=7 Hz; c) singulet at 6.37 ppm; and d) singulet at 7.28 ppm.

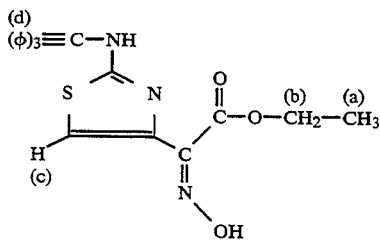

STEP B: Syn isomer of ethyl 2-(2-tritylamino-4-thiazolyl)-2-tetrahydropyranyloxyimino-acetate 2.4 g of p-toluene sulfonic acid were added to a mixture of 5.6 g of the product of Step A in 56 ml of redistilled dihydropyran in an ice bath and the mixture was then stirred for an hour while the temperature returned to room temperature. The mixture was poured into a mixture of 100 ml of benzene, 100 ml of water and 2 ml of triethylamine and the organic phase was decanted, was washed with water, dried and vacuum filtered. The filter was rinsed with benzene and the filtrate was evaporated to dryness. The residue was taken up in isopropyl ether and crystallization was induced. The mixture was stored overnight in a refrigerator and was then vacuum filtered. The product was rinsed with isopropyl ether to obtain 4.42 g of the syn isomer of ethyl 2-(2-tritylamino-4-thiazolyl)-2-tetrahydropyranyloxyimino-acetate melting at 184° C.

Analysis: p-toluene sulfonic acid salt $C_{38}H_{39}O_7N_3S_2$

| | %C | %H | %N | %S |
|---|---|---|---|---|
| Calculated: | 63.9 | 5.5 | 5.9 | 9.0 |
| Found: | 63.7 | 5.5 | 5.8 | 8.9 |

RMN (CDCl$_3$, 60 MHz): a) triplet centered about 1.36 ppm; b) quadruplet centered about 4.39 ppm; c) singulet at 6.60 ppm; d) singulet at 6.91 ppm; and e) singulet at 7.28 ppm.

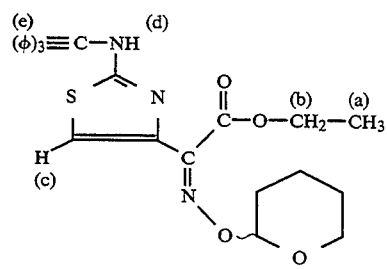

STEP C: syn isomer of 2-(2-tritylamino-4-thiazolyl)-2-tetrahydropyranyloxyimino-acetic acid A mixture of 4.56 g of the product of Step B, 45 ml of dioxane and 8.4 ml of 2N sodium hydroxide was refluxed for 90 minutes and was then cooled on an ice-water bath. The mixture was vacuum filtered and the recovered product was rinsed with aqueous dioxane and then with ether to obtain 4.66 g of a sodium salt. The latter was dissolved in 50 ml of dioxane and the solution was acidified with formic acid to a pH of 5. The addition of 90 ml of water caused precipitation of the syn isomer of 2-(2-tritylamino-4-thiazolyl)-2-tetrahydropyranyloxyimino-acetic acid melting at 180° C.

RMN (CDCl$_3$, 60 MHz): 6.69 ppm (proton of thiazolyl ring) and 7.31 (aromatic).

STEP D: Syn isomer of tert.-butyl 7-[2-(2-tritylamino-4-thiazolyl)-2-tetrahydropyranyloxyimino-acetamido]-3-acetoxymethyl-ceph-3-eme-4-carboxylate A mixture of 0.362 g of the product of Step C, 0.244 g of tert.-butyl 7-amino-3-acetoxymethyl-ceph-3-eme-4-carboxylate, 0.280 g of dicyclohexylcarbodiimide and 4 ml of dry chloroform was stirred for 2 hours at room temperature and the mixture was vacuum filtered to remove dicyclohexylurea which was rinsed with chloroform. The filtrate was evaporated to dryness under reduced pressure and the residue was dissolved in 1 ml of ether. The solution was chromatographed over silica gel and was eluted with ether. The fractions with an Rf=0.38 were combined and evaporated to dryness under reduced pressure. The residue was taken up in isopropyl ether and effloresced. The mixture was vacuum filtered and the recovered product was rinsed with isopropyl ether to obtain 0.184 g of the syn isomer of tert.-butyl 7-[2-(2-tritylamino-4-thiazolyl)-2-tetrahydropyranyloxyimino-acetamido]-3-acetoxymethyl-ceph-3-eme-4-carboxylate.

Analysis: $C_{43}H_{45}O_8N_5S_2$

| | %C | %H | %N | %S |
|---|---|---|---|---|
| Calculated: | 62.7 | 5.5 | 8.5 | 7.8 |
| Found: | 62.8 | 5.9 | 8.1 | 7.5 |

RMN (CDCl$_3$, 60 MHz): a) 1.53 ppm; b) 2.07 ppm; c) 5.46 ppm; d) 6.76 ppm; and e) 7.28 ppm.

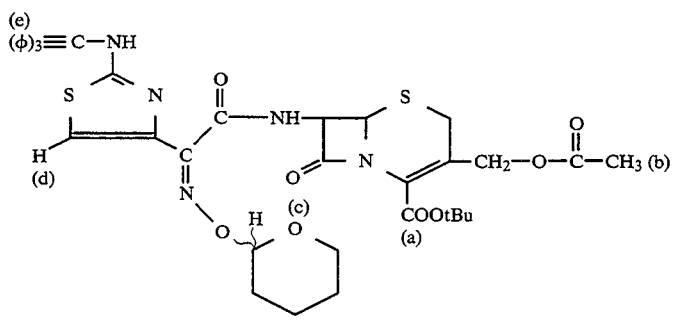

STEP E: Syn isomer of 7-[2-(2-amino-4-thiazolyl)-2-hydroxy-imino-acetamido]-3-acetoxymethyl-ceph-3-eme-4-carboxylic acid A mixture of 638 mg of the product of Step D in 1.8 ml of trifluoroacetic acid was stirred for 15 minutes at room temperature and 18 ml of isopropyl ether was added thereto. The mixture was vacuum filtered to obtain 404 mg of product which was added to 2 ml of 50% aqueous formic acid. The mixture was stirred for 15 minutes at 50° C. and was then evaporated to dryness at 30° C. under reduced pressure. The residue was taken up in 1 ml of of ethanol and after adding a drop of pyridine thereto, the mixture was vacuum filtered to obtain the syn isomer of 7-[2-(2-amino-4-thiazolyl)-2-hydroxyimino-acetamido]-3-acetoxymethyl-ceph-3-eme-4-carboxylic acid which was identical to the product of Example 28.

EXAMPLE 30

Syn isomer of 7-[2-(2-tritylamino-4-thiazolyl)-2-tritylhydroxy-imino-acetamido]-3-acetoxymethyl-ceph-3-eme-4-carboxylic acid

STEP A: Syn isomer of ethyl 2-(2-tritylamino-4-thiazolyl)-2-tritylhydroxyimino-acetate 1.5 ml of triethylamine were added to a solution of 1.08 g of the product of Step A of Example 28 in 8 ml of chloroform and then a solution of 3 g of trityl chloride in 6 ml of chloroform was added thereto at 5° C. over 25 minutes. The mixture was stirred for an hour at room temperature and the mixture was washed with 18 ml of water, then 8 ml of N hydrochloric acid and then 3 times with 20 ml of water. The mixture was dried and evaporated to dryness and the residue was crystallized from isopropanol to obtain 2.3 g of the syn isomer of ethyl 2-(2-tritylamino-4-thiazolyl)-2-tritylhydroxy-imino-acetate melting at 140° C.

STEP B: Sodium salt of syn isomer of 2-(2-tritylamino-4-thiazolyl)-2-tritylhydroxyimino-acetic acid 0.7 g of the product of Step A was dissolved in 3.5 ml of hot dioxane and 1 ml of 2N sodium hydroxide solution was added thereto dropwise with stirring at 110° C. The mixture was stirred for 110 minutes at reflux with stirring and was then cooled and vacuum filtered to obtain the sodium salt of the syn isomer of 2-(2-tritylamino-4-thiazolyl)-2-trityl-hydroxyimino-acetic acid which was identical to Step C of

Example 28

STEP C: Syn isomer of 7-[2-(2-tritylamino-4-thiazolyl)-2-tritylhydroxyimino-acetamido]-3-acetoxymethyl-ceph-3-eme-4-carboxylic acid 50 ml of N hydrochloric acid were added with stirring to a suspension of 5.12 g of the salt of Step B in 50 ml of chloroform and the organic phase was decanted and was washed 3 times with 50 ml of water. The mixture was dried and was vacuum filtered and the filtrate was evaporated to dryness to obtain the syn isomer of 2-(2-tritylamino-4-thiazolyl)-2-tritylhydroxyimino-acetic acid. The said product was dissolved in 50 ml of methylene chloride and 1.6 g of dicyclohexylcarbodiimide were added thereto. The mixture was stirred for an hour at room temperature and was vacuum filtered to remove dicyclohexylurea. The filtrate was cooled to −10° C. and a solution of 1.1 g of 7-amino-cephalosporanic acid in 10 ml of methylene chloride and 1.2 ml of triethylamine was added thereto. The mixture was stirred for 2 hours at room temperature and 50 ml of N hydrochloric acid were added with stirring. The organic phase was decanted, was washed 3 times with 50 ml of water, was dried and vacuum filtered. The filtrate was evaporated to dryness and the residue was effloresced with ethanol. The mixture was filtered to obtain 2.36 g of raw product which was reacted with diethylamine in ether to obtain the diethylamine salt of 7-[2-(2-tritylamino-4-thiazolyl)-2-tritylhydroxyimino-acetamido]-3-acetoxymethyl-ceph-3-eme-4-carboxylic acid. The said salt was dissolved in methylene chloride and N hydrochloric acid was added thereto until the pH was acid. The solution was washed with water, dried and evaporated to dryness to obtain 0.75 g of syn isomer of 7-[2-(2-tritylamino-4-thiazolyl)-2-tritylhydroxyimino-acetamido]-3-acetoxymethyl-ceph-3-eme-4-carboxylic acid.

EXAMPLE 31

7-[2-(2-amino-4-thiazolyl)-2-hydroxyimino-acetamido]-3-acetoxymethyl-ceph-3-eme-4-carboxylic acid A solution of the product of Example 30 in 5 ml of 50% aqueous formic acid was stirred at 50° C. for 15 minutes and was then evaporated to dryness. The residue was taken up in ether and the mixture was vacuum filtered. The product was rinsed with ether to obtain the syn isomer of 7-[2-(2-amino-4-thiazolyl)-2-hydroxyimino-acetamido]-3-acetoxymethyl-ceph-3-eme-4-carboxylic acid in the form of its formate. The latter was triturated with 3 ml of water containing a few drops of pyridine (pH≃6). The mixture was vacuum filtered and the recovered product was rinsed with water and dried to obtain the said acid which was identical to the product of Example 28.

EXAMPLE 32

Sodium salt of syn isomer of
7-[2-(2-amino-4-thiazolyl)-2-hydroxyimino-acetamido]-3-acetoxymethyl-ceph-3-eme-4-carboxylic acid A solution of 0.613 g of the product of Example 28 in 2 ml of distilled water and 2 ml of a M solution of sodium acetate in methanol was admixed with 60 mg of activated carbon and the mixture was vacuum filtered. The filter was rinsed with 2 ml of methanol and the filtrate was evaporated to dryness at 30° C. under reduced pressure. The residue was taken up in ether and was vacuum filtered. The product was dried to obtain 0.432 g of the sodium salt of the syn isomer of 7-[2-(2-amino-4-thiazolyl)-2-hydroxyimino-acetamido]-3-acetoxymethyl-ceph-3-eme-4-carboxylic acid.

EXAMPLE 33

Crystalline sodium salt of the syn isomer of
7-[2-(2-amino-4-thiazolyl)-2-hydroxyimino-acetamido]-3-acetoxymethyl-ceph-3-eme-4-carboxylic acid 8 ml of a molar solution of sodium acetate in methanol were added to a suspension of 1.78 g of the acid of Example 28 in 8 ml of methanol and the sodium salt immediately crystallized. The mixture was stirred for 15 minutes to obtain complete crystallization and was vacuum filtered. The product was washed with ethanol and then with ether to obtain 1.53 g of the crystalline sodium salt of the syn isomer of 7-[2-(2-amino-4-thiazolyl)-2-hydroxyimino-acetamido]-3-acetoxymethyl-ceph-3-eme-4-carboxylic acid as white crystals.

Analysis: $C_{15}H_{14}O_7N_5S_2Na$

| | | | | | | | | | |
|---|---|---|---|---|---|---|---|---|---|
| Calculated: | % C | 38.88 | % H | 3.04 | % N | 15.11 | % S | 13.84 | % Na | 4.96 |
| Found: | | 38.8 | | 3.1 | | 15.1 | | 13.8 | | 4.85 |

Infrared Spectrum (Nujol): C=O at 1753, 1724 and 1683 cm$^{-1}$; —NH and OH at 3597 cm$^{-1}$.

RMN (DMSO, 60 MHz): singulet at 2.01 ppm

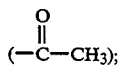

singulet at 6.65 ppm (proton of thiazole ring); and singulet at 7.16 ppm (amine NH$_2$).

EXAMPLE 34

An injectable solution was prepared with 500 mg of 3-acetoxymethyl-7-[2-(2-amino-4-thiazolyl)-2-hydroxyiminoacetamido]-ceph-3-eme-4-carboxylic acid or 3-acetoxymethyl-7-[2-(2-amino-4-thiazolyl)-2-methoxyimino-acetamido]-ceph-3-eme-4-carboxylic acid or the syn isomer of 7-[2-(2-amino-4-thiazolyl)-2-hydroxyimino-acetamido]-3-acetoxymethyl-ceph-3-eme-4-carboxylic acid and sufficient sterile water to make a final solution of 5 ml. A similar solution was prepared with 500 mg of sodium 3-acetoxymethyl-7-[2-(2-amino-4-thiazolyl)-2-methoxyimino)-acetamido]-ceph-3-eme-4-carboxylic acid or 3-acetoxymethyl-7-[2-(2-amino-4-thiazolyl)2-(1-methylethoxyimino)-acetamido]-ceph-3-eme-4-carboxylic acid.

Gelules were prepared with 250 mg of 3-acetoxymethyl 7-[2-(2-amino-4-thiazolyl)-2-methoxyimino-acetamido]-ceph-3-eme-4-carboxylic acid or sodium 3-acetoxymethyl-7-[2-(2-amino-4-thiazolyl)-2-methoxyimino-acetamido]-ceph-3-eme-4-carboxylate or 3-acetoxymethyl-7-[2-(2-amino-4-thiazolyl)-2-(1-methylethoxyimino)-acetamido]-ceph-3-eme-4-carboxylic acid or the syn isomer of 7-[2-(2-amino-4-thiazolyl)-2-hydroxyimino-acetamido]-3-acetoxymethyl-ceph-3-eme-4-carboxylic acid and sufficient excipient to obtain a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 to 48 hours at 37° C. in an oven. The increasing inhibition was determined by transillumination to determine the minimum inhibiting concentration (MIC in μg/ml) and the results are reported in the follow Tables.

Product A is the anti isomer of 3-acetoxymethyl-7-[2-(2-amino-4-thiazolyl)-2-methoxyimino-acetamido]-ceph-3-eme-4-carboxylic acid.

| iminoacetamido]-ceph-3-eme-4-carboxylic acid | | |
|---|---|---|
| | M.I.C. in μg/ml | |
| STRAINS | 24 H | 48 H |
| Staphylococcus aureus UC 1061 Pen-Sensible | 5 | 5 |
| Staphylococcus aureus UC 1128 Pen-Resistant | 10 | 10 |
| Staphylococcus aureus Exp. N° 54146 | 5 | 10 |
| Streptococcus pyogenes A 561 | 0,5 | 0,5 |
| Bacillus subtilis ATCC 6633 | 2 | 5 |
| Escherichia Coli ST UC 1020 | 3 | 3 |
| Escherichia Coli RT UC 1261 | 1 | 1 |
| Escherichia Coli Exp. TO$_{26}$B$_6$ | 2 | 2 |
| Escherichia Coli RG R55 123D | 5 | 10 |
| Klebsiella pneumoniae Exp. 52145 | 0,6 | 0,6 |
| Klebsiella pneumoniae 2536 R | 20 | 40 |
| Proteus mirabilis (indol—) A 235 | 2 | 2 |
| Salmonella typhimurium 420 | 2 | 2 |
| Enterobacter cloacae 681 | 40 | 40 |

| | M.I.C. in pg/ml | |
|---|---|---|
| STRAINS | 24 H | 48 H |
| Staphylococcus aureus UC 1061 Pen-Sensible | 5 | 5 |
| Staphylococcus aureus UC 1129 Pen-Resistant | 10 | 10 |
| Staphylococcus aureus Exp. N° 54146 | 5 | 5 |
| Streptococcus pyogenes A 561 | 0,5 | 0,5 |
| Bacillus subtilis ATCC 66331 | 2 | 5 |
| Escherichia Coli ST UC 1020 | 3 | 3 |
| Escherichia Coli RT UC 1261 | 1 | 1 |
| Escherichia Coli Exp. TO$_{26}$B$_6$ | 2 | 2 |
| Escherichia Coli RG R55 123D | 5 | 10 |
| Klebsiella pneumoniae exp. 52145 | 0,6 | 0,6 |
| Klebsiella pneumoniae 2536 R | 20 | 40 |
| Proteus mirabilis (indol—) A 235 | 2 | 2 |
| Salmonella typhimurium 420 | 2 | 2 |
| Enterobacter cloacae 681 | 40 | 40 |
| Proteus vulgaris (indol+) A 232 | 2 | 10 |
| Salmonella typhimarium 420 | 1 | 10 |
| Providencia DU 4S | 3 | 5 |
| Pseudomonas 3 935 Exp. SG | 20 | 20 |
| Serratia Resistant Gentamicine 2 532 | 0,4 | 1 |

| STRAINS | Product of Example 4 M.I.C. in µg/ml | | Product of Example 7 M.I.C. in µg/ml | | Product A M.I.C. in µg/ml | |
|---|---|---|---|---|---|---|
| | 24 H | 48 H | 24 H | 48 H | 24 H | 48 H |
| *Escherichia Coli* Resistant Tetracycline ATCC 11 303 = UC 1261 | 0,02 | 0,02 | ≦0,02 | ≦0,02 | 2 | 2 |
| *Escherichia Coli* Exp. T0$_{26}$B$_6$ | 0,1 | 0,1 | 0,05 | 0,05 | 5 | 5 |
| *Escherichia Coli* Resistant Gentamicine, Tobramycine R 55 123 D | 0,6 | 0,6-1 | 0,1 | 0,1 | 10 | 10 |
| *Klebsiella pneumoniae* Exp. 52 145 | 0,02 | 0,02 | ≦0,02 | ≦0,02 | 1 | 1 |
| *Klebsiella pneumoniae* 2 536 Resistant Gentamicine | 0,6 | 0,6 | 0,2 | 0,2 | >40 | >40 |
| *Proteus mirabilis* (indol−) A 235 | 0,02 | 0,02 | ≦0,02 | ≦0,02 | 2 | 2 |
| *Proteus vulgaris* (indol+) A 232 | 2 | 40 | 0,2 | 0,6 | >40 | >40 |
| *Salmonella typhimurium* 420 | 0,2 | 0,2 | 0,1 | 0,1 | 20 | 20 |
| *Providencia* Du 48 | 5 | 5 | 1 | 2 | 40 | >40 |
| *Pseudomonas* 3 935 Exp. SG | 10 | 40 | 10 | 20 | >40 | >40 |
| *Serratia* Resistant Gentamicine 2 532 | 1 | 1 | 1 | 1 | >40 | >40 |
| *Enterobacter cloacae* 681 | 40 | 40 | | | | |
| *Pseudomonas* 8951 RGT | 40 | >40 | | | | |
| *Staphylococcus* Smith | 1 | 1 | | | | |
| *Escherichia Coli* Galle | 0,1 | 0,2 | | | | |
| *Escherichia Coli* E$_6$ | 0,05 | 0,05 | | | | |
| *Escherichia Coli* T 25 575 | 0,05 | 0,05 | | | | |
| *Escherichia Coli* T 96 875 | 0,05 | 0,05 | | | | |

| STRAINS | Product of Example 9 M.I.C. in µg/ml | |
|---|---|---|
| | 24 H | 48 H |
| *Staphylococcus aureus* ATCC 5 638 Pen-Sensible | 1 | 2 |
| *Staphylococcus aureus* UC 1 128 Pen-Resistant | 2 | 2 |
| *Staphylococcus aureus* exp. n° 54 146 | 2 | 2 |
| *Staphylococcus aureus* Co 15 Resistant Cephalexine | 10 | 20 |
| *Streptococcus pyogenes* A 561 | 0,02 | 0,02 |
| *Streptococcus faecalis* 5 432 | 2 | 10 |
| *Bacillus subtilis* ATCC 6 633 | 1 | 1 |
| *Escherichia Coli* Sensible Tetracycline ATCC 9 637 | 1 | 1 |
| *Escherichia Coli* Resistant Tetracycline ATCC 11 303 | 0,1 | 0,1 |
| *Escherichia Coli* Exp. T0$_{26}$B$_6$ | 1 | 1 |
| *Escherichia Coli* Resistant Gentamicine, Tobramycine R 55 123 D | 1 | 1 |

-continued

| STRAINS | Product of Example 9 M.I.C. in µg/ml | |
|---|---|---|
| | 24 H | 48 H |
| *Klebsiella pneumoniae* Exp. 52 145 | 0,05 | 0,1 |
| *Klebsiella pneumoniae* 2 536 Resistant Gentamicine | 2 | 5 |
| *Proteus mirabilis* (indol−) A 235 | 0,2 | 0,2 |
| *Proteus vulgaris* (indol+) A 232 | 2 | 10 |
| *Salmonella typhimurium* 420 | 1 | 10 |
| *Providencia* DU 4S | 3 | 5 |
| *Pseudomonas* 3 935 Exp. SG | 20 | 20 |
| *Serratia* Resistant Gentamicine 2 532 | 0,4 | 1 |

| STRAINS | Product of Example 11 M.I.C. in µg/ml | | Product of Example 15 M.I.C. in µg/ml | | Product of Example 13 M.I.C. in µg/ml | | Product of Example 17 M.I.C. in µg/ml | |
|---|---|---|---|---|---|---|---|---|
| | 24 H | 48 H | 24 H | 48 H | 24 H | 48 H | 24 H | 48 H |
| *Staphylococcus aureus* ATCC 5 638 Pen-Sensible | 2 | 2 | 20 | 20 | 2 | 5 | 20 | 20 |
| *Staphylococcus aureus* UC 1 128 Pen-Resistant | 2 | 3 | 40 | 40 | 3 | 5 | 40 | 40 |
| *Staphylococcus aureus* exp, n° 54 146 | 2 | 2 | 40 | 40 | 2 | 5 | 40 | 40 |
| *Streptococcus pyogenes* A 561 | 0,02 | 0,02 | 0,4 | 0,4 | 0,02 | 0,02 | 1 | 1 |
| *Streptococcus faecalis* 5 432 | 2 | 10 | >100 | >100 | 5 | 40 | >100 | >100 |
| *Streptococcus faecalis* 99 F 74 | 2 | 20 | >100 | >100 | 5 | 20 | >100 | >100 |
| *Bacillus subtilis* ATCC 6 633 | 0,4 | 0,4 | 10 | 10 | 0,5 | 2 | 20 | >100 |
| *Escherichia Coli* Sensible Tetracycline ATCC 9 637 | 1 | 1 | >100 | >100 | 2 | 2 | >100 | >100 |
| *Escherichia Coli* Resistant Tetracycline ATCC 11 303 | ≦0,2 | 0,2 | 10 | 10 | 0,5 | 0,5 | 20 | 20 |
| *Escherichia Coli* Exp. T0$_{26}$B$_6$ | 0,4 | 0,4 | 20 | 40 | 1 | 1 | 100 | 100 |
| *Escherichia Coli* Resistant Gentamicine, Tobramycine R 55 123 D | 0,6 | 0,6 | 40 | 40 | 1 | 1 | 100 | 100 |
| *Klebsiella pneumoniae* Exp. 52 145 | 0-05 | 5 | 20 | 20 | 0,2 | 0,2 | 40 | 40 |
| *Klebsiella pneumoniae* 2 536 Resistant Gentamicine | 2 | 2 | >100 | >100 | 10 | 10 | >100 | >100 |
| *Proteus mirabilis* (indol−) A 235 | 0,05 | 5 | 5 | 5 | 0,5 | 0,5 | 10 | 20 |
| *Proteus vulgaris* (indol+) A 232 | 1 | 2 | >100 | >100 | 0,5 | 1 | >100 | >100 |
| *Salmonella typhimurium* 420 | 1 | 1 | 100 | 100 | 2 | 2 | 100 | 100 |
| *Providencia* Du 48 | 5 | 5 | 100 | >100 | 5 | 5 | >100 | >100 |
| *Pseudomonas* 3 935 Exp. SG | 20 | 40 | >100 | >100 | 40 | 40 | >100 | >100 |
| *Serratia* Resistant Gentamicine 2 532 | 2 | 2 | >100 | >100 | 2 | 5 | >100 | >100 |

| PRODUCT OF EXAMPLE 28 | | |
|---|---|---|
| | M.I.C. in µg/ml | |
| Strain | 24 H | 48 H |
| *Staphylococcus aureus* UC 6 538 Pen-Sensible | 0.5 | 0.5 |
| *Staphylococcus aureus* UC 1 128 Pen-Resistant | 1 | 1 |
| *Staphylococcus aureus* exp. No 54 146 | 1 | 1 |
| *Streptococcus pyogenes* A 561 | 0.02 | 0.02 |
| *Streptococcus faecalis* 5 432 | 5 | 5 |
| *Streptococcus faecalis* 99 F 74 | 10 | 40 |
| *Bacillus subtilis* ATCC 6 633 | 0.5 | 1 |
| *Escherichia Coli* Sensible Tetracycline ATCC 9 637 | 0.05 | 0.1 |
| *Escherichia Coli* Resistant Tetracycline ATCC 11 303 | 0.1 | 0.1 |
| *Escherichia Coli* Exp. T$O_{26}B_6$ | 0.05 | 0.1 |
| *Escherichia Coli* Resistant Gentamicine Tobramycine R 55 123 D | 0.2 | 0.2 |
| *Klebsiella pneumoniae* Exp. 52 145 | 0.05 | 0.1 |
| *Klebsiella pneumoniae* 2 536 | 0.2 | 0.5 |
| Resistant Gentamicine | | |
| *Proteus mirabilis* (indol—) A 235 | 0.1 | 0.2 |
| *Salmonella typhimurium* 420 | 0.1 | 0.1 |
| *Enterobacter cloacae* 681 | 5 | 10 |
| *Providencia* DU 48 | 2 | 2 |
| *Serratia* Resistant Gentamicine 2 532 | 5 | 10 |

B. Experimental Infection with *Escherichia coli* (T) $O_{26}B_6$

The product of Example 4 was studied for its activity against an experimental infection of *Escherichia coli* in groups of 10 male mice weighing about 21.5 g. The mice received an intraperitoneal injection of 0.5 ml of a 24 hour old culture in a nutritive media of *Escherichia coli* (T) $O_{26}B_6$ of the Pasteur Institute diluted 1/6 with distilled water. The test product was administered subcutaneously or orally 1 hour and 5 and 24 hours after the infection and the number of dead was determined after 8 days. The results are reported in the following Table.

| | Mortality After | | | mice alive after |
|---|---|---|---|---|
| Dose in mg | 21½ H | 28½ H | 32 H | 8 days |
| Controls | 9 | | 1 | 0/10 |
| 0.05 subcutaneously | | | | 10/10 |
| 0.1 subcutaneously | | | | 10/10 |
| 0.25 subcutaneously | | | | 10/10 |
| 0.1 subcutaneously | | | | 10/10 |
| 0.1 orally | | 1 | | 9/10 |
| 0.25 orally | | | | 10/10 |
| 0.5 orally | | | | 10/10 |

The procedure was repeated with mice weighing about 22.5 g with an intraperitoneal injection of a 24 hour old culture of *Escherichia coli* (T) $O_{26}B_6$ diluted 1/5.5 with distilled water with the product of Example 4. The results are reported in the following Table.

| | | MORTALITY AFTER | | | | | | | | | | |
|---|---|---|---|---|---|---|---|---|---|---|---|---|
| Dose in mg | Method of Treatment | 7 H 45 | 9 H 35 | 22 H 30 | 23 H 50 | 24 H | 25 H 50 | 26 H 30 | 31 H | 32 H | 46 H 30 | 70 H | 4 j | Mice alive on the 8th day |
| Controls | | | | | | | | | | | | | | |
| 3 × 0,5 ml of eau | S.C. | 1 | 1 | 8 | | | | | | | | | | 0/10 |
| 0,015 | S.C. | | | 2 | 2 | | | | | | 2 | | | 4/10 |
| 0,025 | S.C. | | | | | | 1 | 1 | | | | 2 | | 6/10 |
| 0,05 | S.C. | | | | | | | | | | | | | 10/10 |
| 0,05 | OS | | | 4 | | 1 | | | 1 | 2 | | | | 2/10 |
| 0,1 | OS | | 1 | | | 1 | | | | 2 | | 1 | | 5/10 |
| 0,25 | OS | | | | | | | | | | | | | 10/10 |

C. Experimental Infection with *Salmonella typhimurium*

Groups of 10 mice with an average weight of 20.5 g were intraperitoneally injected with 0.5 ml of a 24 hour old culture in oxoid bouillon of *Salmonella typhimurium* 5210 diluted 1/75 with distilled water. The product of Example 7 was administered subcutaneously one hour and 4,8,24 and 32 hours after the infection and the results, determined as before, are reported in the following Table.

| | MORTAL AFTER | | | | | | | |
|---|---|---|---|---|---|---|---|---|
| Dose in mg Controls | 21 H 30 | 25 H | 28 H | 29 H | 45 H 30 | 56 H | 70 H | Mice alive on the 10th day |
| 0,1 | 1 | 1 | 1 | 1 | 1 | 1 | 4 | 0/10 |
| 0,25 | | | | | | | | |
| 0,5 | | | | | | | | |
| 1 | | | | | | | | |
| 2 | | | | | | | | |

| Dose in mg Controls | 4J | 5J | 6J | 7J | 8J | 9J | Mice alive on the 10th day |
|---|---|---|---|---|---|---|---|
| 0,1 | | | 3 | 3 | 1 | | 3/10 |
| 0,25 | | | | 2 | 1 | 2 | 5/10 |
| 0,5 | | 1 | 1 | 1 | | | 7/10 |
| 1 | | | | | 1 | | 9/10 |
| 2 | | | | | | | 10/10 |

D. Experimental infection of *Proteus mirabilis*

Groups of 10 mice with an average weight of 22 g received intraperitoneally 0.5 ml of a 24 hour old culture in oxoid bouillon of *Proteus mirabilis* A 235 diluted ¼ with distilled water. The mice then received subcutaneously the compound of Examples 11 or 15 one hour and 5 and 24 hours after the infection and the results are reported in the following Table.

| Dose in mg | Product of Examples | 6 H 55 | 21 H 30 | 22 H 15 | 23 H 10 | 23 H 30 | 23 H 45 | 24 H 20 | 28 H | 29 H | 31 H 45 | 46 H | 53 H | 70 H | 94 H | Mice alive on the 8th day |
|---|---|---|---|---|---|---|---|---|---|---|---|---|---|---|---|---|
| Controls |  | 1 | 9 |  |  |  |  |  |  |  |  |  |  |  |  | 0/10 |
| 0.025 | 11 |  | 3 | 1 |  |  |  | 1 | 2 |  |  | 2 | 1 |  |  | 0/10 |
| 0.05 | 11 |  |  | 1 |  |  |  | 1 |  |  | 1 |  |  | 2 |  | 5/10 |
| 0.1 | 11 |  |  |  |  |  |  |  | 1 |  |  | 2 |  |  |  | 7/10 |
| 0.25 | 11 |  |  |  |  |  |  |  |  |  |  |  |  |  |  | 10/10 |
| 0.5 | 11 |  |  |  |  |  |  |  |  |  |  |  |  |  |  | 10/10 |
| 1 | 11 |  |  |  |  |  |  |  |  |  |  |  |  |  |  | 10/10 |
| 0.5 | 15 | 1 | 9 |  |  |  |  |  |  |  |  |  |  |  |  | 0/10 |
| 1 | 15 |  | 5 |  | 1 | 1 |  | 2 |  |  |  |  |  |  | 1 | 0/10 |

E. Acute Toxicity

The acute toxicity of the product of Example 7 was determined on groups of 8 to 10 female mice of Swiss CD1 Specific Pathogen Free Strain (stock CH.River-France), with an average weight of 19 to 21 g, for each dose of the compound.

The animals had injection in the caudal vein in a variable volume at a rate of 1 ml/mn of the product of Example 7 dissolved at a concentration of 100 mg/ml in sterile apyrogen distilled water. The animals were observed for 4 days with food and drinking water "ad libitum" at a temperature of 21° ± 1° C., constant humidity and area with excess air pressure. The results are reported in the following Table.

| Dose in mg | Total Mortality |
|---|---|
| 500 | 0/10 |
| 1000 | 0/10 |
| 2000 | 0/8 |

The lethal dose of the compound of Example 7 is therefore above 2000 mg/kg.

Symptomatology

No symptoms of intoxication were noted following the injections nor during the observation period.

Various modifications of the products and processes of the invention may be made without departing from the spirit or scope thereof and it should be understood that the invention is to be limited only as defined in the appended claims.

We claim:

1. A syn isomer of a compound of the formula

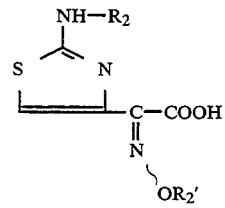

wherein $R_2$ is selected from the group consisting of hydrogen and a group easily removable by acid hydrolysis or hydrogenolysis and $R_2'$ is selected from the group consisting of hydrogen, alkyl of 1 to 4 carbon atoms, alkenyl and alkynyl of 2 to 4 carbon atoms and a group easily removable by acid hydrolysis or hydrogenolysis with the proviso that $R_2'$ is not hydrogen when $R_2$ is other than hydrogen.

* * * * *

Disclaimer 5,336,776—Rene' Heymes, Romainville; Andr Lutz, Strasbourg, both of France. NOVEL 3-ACETOXYM-ETHYL-7-(IMINOACETAMIDO)-CEPHALOSPORANIC ACID. Patent dated August 9, 1994. Disclaimer filed on August 1, 2002, by Assignee.

The term of this patent shall not extend beyond the expiration date of Patent No. 4,376,203.

*(Official Gazette, July 22, 2003)*